United States Patent [19]

Tanaka et al.

[11] 4,233,309
[45] Nov. 11, 1980

[54] NOVEL 1-SUBSTITUTED-3-ACYLPYRROLE DERIVATIVES, PLATELET AGGREGATION INHIBITORS CONTAINING THEM, AS ACTIVE INGREDIENTS, AND PROCESSES FOR PRODUCTION OF SAID DERIVATIVES

[75] Inventors: Toshio Tanaka; Akira Otsu; Seizi Kurozumi, all of Hino; Toshio Wakabayashi, Tama, all of Japan

[73] Assignee: Teijin Limited, Osaka, Japan

[21] Appl. No.: 966,050

[22] Filed: Dec. 4, 1978

[30] Foreign Application Priority Data

Dec. 6, 1977 [JP] Japan .................. 52-145702
Jan. 10, 1978 [JP] Japan ...................... 53-801

[51] Int. Cl.³ .................... C07D 207/00; A61K 31/40
[52] U.S. Cl. ........................... 424/270; 260/326.5 J
[58] Field of Search ............... 260/326.43, 326.5 J; 424/274

[56] References Cited

U.S. PATENT DOCUMENTS 3,551,571  12/1970  Pachter et al. ............... 424/274
3,644,631  2/1972   Pachter et al. ............... 424/274

FOREIGN PATENT DOCUMENTS 1168941  10/1969  United Kingdom.

Primary Examiner—Jose Tovar
Attorney, Agent, or Firm—Wenderoth, Lind & Ponack

[57] ABSTRACT

Novel 1-substituted-3-acylpyrrole derivatives of the formula

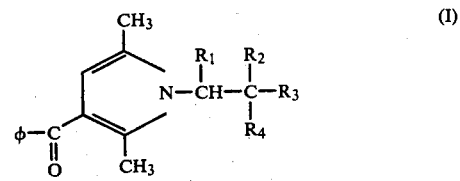

(I)

wherein all symbols are as defined in the specification; and platelet aggregation inhibiting agents comprising them as active ingredients. These novel 1-substituted-3-acylpyrrole derivatives are prepared by condensing the corresponding 1-substituted pyrrole derivatives with the corresponding acylating agents in the presence of acid catalysts, and if desired, subjecting the products to oxidation, hydrolysis, amidation or acetal-forming reaction. These 1-substituted-3-acylpyrrole derivatives exhibit unique properties in that they have superior platelet aggregation inhibiting actions with low antiinflammatory activity.

3 Claims, No Drawings

NOVEL 1-SUBSTITUTED-3-ACYLPYRROLE DERIVATIVES, PLATELET AGGREGATION INHIBITORS CONTAINING THEM, AS ACTIVE INGREDIENTS, AND PROCESSES FOR PRODUCTION OF SAID DERIVATIVES

This invention relates to novel 1-substituted-3-acylpyrrole derivatives, platelet aggregation inhibiting agents containing said derivatives as active ingredients, and to processes for preparing said pyrrole derivatives.

Indomethacine, conventionally known as a typical antiinflammatory agent, contains an acyl-substituted pyrrole ring as part of its structure, and many acylated pyrrole derivatives have been prepared by utilizing this fact. The 1-substituted-3-acylpyrrole derivatives of the invention to be described hereinbelow have not been known previously.

The investigations of the present inventors have shown that novel 1-substituted-3-acylpyrrole derivatives described below can be synthesized, and these pyrrole derivatives have an action of inhibiting platelet aggregation.

[COMPOUNDS]

The novel 1-substituted-3-acylpyrrole derivatives of the invention are expressed by the following formula [I].

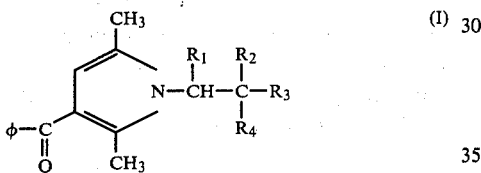

wherein $\phi$ represents a phenyl group which may be substituted by 1 or 2 halogen atoms, hydroxyl groups, carboxyl groups, alkoxycarbonyl groups with 2 to 4 carbon atoms, alkyl or alkoxy groups with 1 to 3 carbon atoms, or acyloxy groups with 2 to 4 carbon atoms which substituents being the same or different; a cycloaklyl or cycloalkenyl group with 5 or 6 carbon atoms; a branched alkyl group with 3 to 5 carbon atoms; or a 5- or 6-membered heterocyclic group containing 1 or 2 nitrogen, sulfur or oxygen atoms which are the same or different as hetero atoms, which heterocyclic ring may be substituted by 1 to 2 halogen atoms, hydroxyl groups, carboxyl groups, alkoxycarbonyl groups with 2 to 4 carbon atoms, alkyl or alkoxy groups with 1 to 3 carbon atoms or acyloxy groups with 2 to 4 carbon atoms, said substituents being the same or different;

$R_1$ represents a hydrogen atom or a lower alkyl group with 1 to 4 carbon atoms; and $R_2$, $R_3$ and $R_4$ are difined by any one of (1), (2) and (3) below, (1) $R_2$ represents the group —X—$R_6$ in which X represents an oxygen or sulfur atom or a sulfinyl or sulfonyl group and $R_5$ represents a hydrogen atom, a lower alkyl group with 1 to 4 carbon atoms, a phenyl or benzyl group which may be substituted by a hydroxyl group, a carboxyl group, an alkoxycarbonyl or acyloxy group with 2 to 4 carbon atoms, or an acyl group with 2 to 10 carbon atoms, and $R_3$ and $R_4$ may be the same or different and each represent a hydrogen atom, a lower alkyl group with 1 to 4 carbon atoms, or a phenyl group which may be substituted by a hydroxyl group, a carboxyl group, or by an alkoxycarbonyl or acyloxy group with 2 to 4 carbon atoms;

(2) $R_2$ and $R_3$ together represent =O; and $R_4$ represents a hydrogen atom, a lower alkyl or alkoxy group with 1 to 4 carbon atoms, a phenoxy or benzyloxy group which may be substituted by one or two halogen atoms, hydroxyl groups, carboxyl groups, alkoxycarbonyl groups with 2 to 4 carbon atoms, aklyl groups or alkoxy groups with 1 to 3 carbon atoms, or acyloxy groups with 2 to 4 carbon atoms, said substituents being the same or different, an amino group, a hydrazino group, an amino or hydrazino group substituted by 1 or 2 lower alkyl groups with 1 to 4 carbon atoms or 1 or 2 phenyl groups, an amino group substituted by 1 or 2 $\beta$-hydroxyethyl groups, or a 5- or 6-membered alkyleneamino group which may contain one oxygen atom as a hetero atom; or (3) $R_2$ and $R_3$ each represent an alkoxy group with 1 to 4 carbon atoms or together represent an ethylenedioxy group; and $R_4$ represents a hydrogen atom or a lower alkyl group with 1 to 4 carbon atoms.

It has previously been known that 3-acyl-1-substitued pyrrole derivatives of the following formula

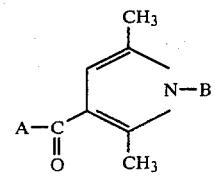

wherein A represents an aryl group, a substituted aryl group, or a heteroaromatic monocyclic group, and B represents a lower alkyl group or a substituted or unsubstituted phenyl or benzyl have antiinflammatory, analgesic and antipyretic activities (see, for example, U.S. Pat. Nos. 3,551,571 and 3,644,631, and British Pat. No. 1,161,638).

The pyrrole derivatives of formula (I) differ from the known 3-acyl-1-substituted pyrrole derivatives in that the N-substituent at the 1-position has an alcoholic hydroxyl group, an ether group, a thioether group, or functional groups derived from oxidation of these groups, as expressed by —X—$R_5$, through two straight-chain carbon atoms. The pyrrole derivatives of the invention have unique pharmacological actions in that they have low antiinflammatory activities and high platelet aggregation inhibiting activities.

U.S. Pat. No. 3,530,115 and British Pat. No. 1,168,941 disclose penicillin derivatives containing as an acyl group a pyrrole derivative residue having a carbonyl residue at the 1 1-position which is of a similar structure to the 3-acyl-1-substituted pyrrole derivatives of the invention, but are quite silent on the pharmacological activities of such pyrrole derivatives themselves.

The structures of groups $R_2$, $R_3$ and $R_4$, especially $R_2$, in formula (I) are particularly important in the structure of the 1-substituted-3-acylpyrrole derivatives of the present invention. The pyrrole derivatives of the invention are therefore described in greater details by reference to these groups.

(1) When $R_2$ represents the group —X—$R_5$:

In this case, the 1-substituted-3-acylpyrrole derivatives of the invention are expressed by the following formula

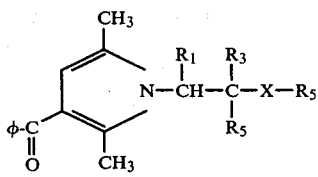
(I-1)

wherein all symbols are as defined in formula (I). Depending upon the definitions of groups —X— and R₅, pyrrole derivatives of this type (I-1) include those of the following three sub-types.

(1) Pyrrole derivatives of the following formula

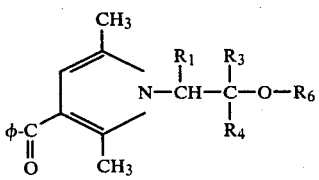
(I-1a)

wherein $\phi$, $R_1$, $R_3$ and $R_4$ are as defined in formula (I), and $R_6$ represents a hydrogen atom, a lower alkyl group with 1 to 4 carbon atoms, or a phenyl or benzyl group which may be substituted by a hydroxyl group, a carboxyl group or an alkoxycarbonyl or acyloxy group with 2 to 4 carbon atoms.

The pyrrole derivatives of formula (I-1a) are characterized in that the substituent at the nitrogen atom at the 1-position includes an alcoholic hydroxyl group or an ether group. Those in which $R_6$ represents a lower alkyl group with 1 to 4 carbon atoms, especially a methyl groups, are especially suitable.

(2) Pyrrole derivatives of the following formula

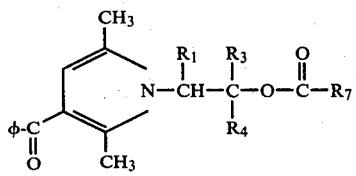
(I-1b)

wherein $\phi$, $R_1$, $R_3$ and $R_4$ are as defined in formula (I), and $R_7$ represents a hydrocarbon residue containing 1 to 9 carbon atoms. The pyrrole derivatives of formula (I-1b) are characterized in that the substituent at the nitrogen atom at the 1-position includes an acyloxy group. The pyrrole derivatives of sub-type (I-1b) also exhibit good platelet aggregation inhibiting activities.

(3) Pyrrole derivatives of the formula

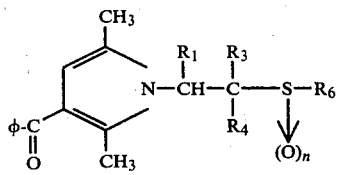
(I-1c)

wherein $\phi$, $R_1$, $R_3$ and $R_4$ are as defined in formula (I), and $R_6$ is as defined in formula (I-1a), n is 0, 1 or 2, and

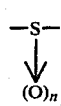

represents a sulfur atom when n is 0, a sulfinyl group when n is 1, and a sulfonyl group when n is 2. These pyrrole derivatives of the invention having the formula (I-1c) are characterized in that the substituent at the nitrogen atom at the 1-position includes a thiol, thioether, sulfinyl or sulfonyl group.

(2) When $R_2$ and $R_3$ together represent =O:

In this case, the 1-1-substituted 3-acylpyrrole derivatives of the invention are expressed by the following formula

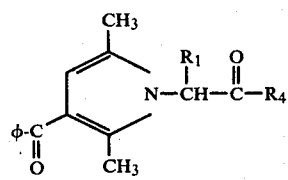
(I-2)

wherein all symbols are as defined in formula (I). Depending upon the definition of the group $R_4$, pyrrole derivatives of this type includes those of the following four sub-types.

(4) Pyrrole derivatives of the formula

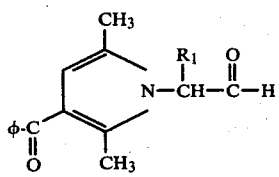
(I-2a)

wherein $\phi$ and $R_1$ are as defined in formula (I). The pyrrole derivatives of this sub-type (I2a) are characterized in that the substituent at the nitrogen atom at the 1-position includes a formyl group.

(5) Pyrrole derivatives of the following formula

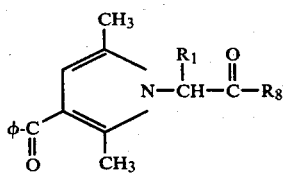
(I-2b)

wherein $\phi$ and $R_1$ are as defined in formula (I), and $R_8$ represents a lower alkyl group with 1 to 4 carbon atoms. The pyrrole derivatives of this sub-type (I-2b) are characterized in that the substituent at the nitrogen atom at the 1-position includes an acyl group. Those in which $R_8$ represents a methyl or ethyl group are especially suitable.

(6) Pyrrole derivatives of the following formula

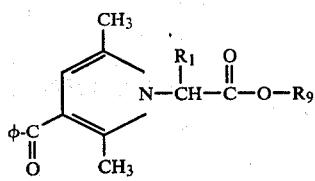

wherein φ and $R_1$ are as defined in formula (I), and $R_9$ represents an alkyl group with 1 to 4 carbon atoms, or a phenyl or benzyl group which may be substituted by 1 or 2 halogen atoms, hydroxyl groups, carboxyl groups, alkoxycarbonyl groups with 2 to 4 carbon atoms, alkyl or alkoxy groups with 1 to 3 carbon atoms or acyloxy groups with 2 to 4 carbon atoms, said substituents being the same or different. The pyrrole derivatives of this sub-type (I-2c) are characterized in that the nitrogen atom at the 1-position is substituted by a substituent having an ester group. These pyrrole derivatives (I-2c) have good platelet aggregation inhibiting activity.

(7) Pyrrole derivatives of the following formula

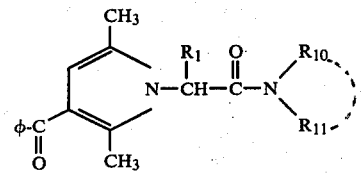

wherein φ and $R_1$ are as defined in formula (I), and $R_{10}$ and $R_{11}$ are the same or different and each represent a hydrogen atom, a lower alkyl group with 1 to 4 carbon atoms, a phenyl group, a β-hydroxyethyl group, an amino group or an amino group substituted by 1 or 2 lower alkyl groups with 1 to 4 carbon atoms, or $R_{10}$ and $R_{11}$ together form a 5- or 6-membered alkylene group which may contain one oxygen atom as a hetero atom. The pyrrole derivatives of the sub-type (I-2d) are characterized in that the nitrogen atom at the 1-postion has an amido or hydrazido group. Those in which the nitrogen atom at the 1-position contains an amido group are especially suitable.

(3) When $R_2$ and $R_3$ each represent an alkoxy group or together represent an ethylenedioxy group:

In this case, the 1-substituted-3-acylpyrrole derivatives of the invention are expressed by the following formula

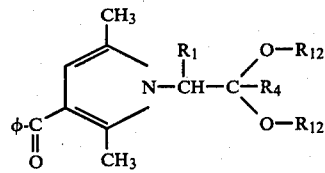

wherein φ, $R_1$ and $R_4$ are as defined in formula (I), and $R_{12}$ groups each represent an alkyl group with 1 to 4 carbon atoms or together represent an ethylene group. The pyrrole derivatives of this type (I-3) correspond to the acetals of the pyrrole derivatives of formulae (I-2a) and (I-2b), and exhibit equally good activities of inhibiting platelet aggregation.

The 1-substituted-3-acylpyrrole derivatives of formula (I) can be structurally classified, as mentioned above, into the three types and eight sub-types according to the groups $R_2$, $R_3$ and $R_4$, especially $R_2$. These types and sub-types, however, are common in that they have groups such as an alcoholic hydroxyl group or functional groups derived from its oxidation, as expressed by —X—$R_5$, through two straight-chain carbon atoms, and equally have good activities of inhibiting platelet aggregation.

Among the 1-substituted-3-acylpyrrole derivatives of formula (I) of the invention, those in which φ is a phenyl group, and $R_1$ represents a lower alkyl group with 1 to 4 carbon atoms, particularly a methyl group, are especially preferred. The α-carbon atom to which the group $R_1$ is attached is an asymmetric carbon atom. The 1-substituted-3-acylpyrrole derivatives of formula (I) of the invention include not only racemic mixtures but also optically active isomers.

Preferred groups of compounds of formula (I) are those of formulae (I-1a) and I-1b) which have especially superior activities of inhibiting platelet aggregation.

Specific examples of the 1-substituted-3-acylpyrrole derivatives of the invention are given below by sub-types.

(1) Pyrrole derivatives of formula (I-1a) containing an alcoholic hydroxyl group or an ether group as a substituent:

(100), 2-(3-benzoyl-2,5-dimethylpyrrol-1-yl)-ethanol,
(102), 2-(3-benzoyl-2,5-dimethylpyrrol-1-yl)-1-methylethanol,
(104), 2-(3-benzoyl-2,5-dimethylpyrrol-1-yl)-1-ethylethanol,
(106), 2-(3-benzoyl-2,5-dimethylpyrrol-1-yl)-2-methylethanol,
(108), (2S)-2-(3-benzoyl-2.5-dimethylpyrrol-1-yl)-2-methylethanol,
(110), (2R)-2-(3-benzoyl-2,5-dimethylpyrrol-1-yl)-2-methylethanol,
(112), 2-(3-benzoyl-2,5-dimethylpyrrol-1-yl)-2-ethylethanol,
(114), 2-(3-benzoyl-2,5 -dimethylpyrrol-1-yl)-2-isopropylethanol,
(116), 2-(3-benzoyl-2,5-dimethylpyrrol-1-yl)-2-isobutylethanol,
(118), 2-(3-benzoyl-2,5-dimethylpyrrol-1-yl)-2-methyl-1-phenylethanol,
(120), 2-(3-p-chlorobenzoyl-2,5-dimethylpyrrol-1-yl)-ethanol,
(122), 2-(3-o-methylbenzoyl-2,5-dimethylpyrrol-1-yl)-2-methylethanol,
(124), 2-methyl-2-[3-(2-thenoyl)-2,5-dimethylpyrrol-1-yl]-ethanol,
(126), 2-methyl-2-(3-nicotinoyl-2,5-dimethylpyrrol-1-yl)-ethanol,
(128), 2-(3-cyclohexylcarbonyl-2,5-dimethylpyrrol-1-yl)-2-methylethanol,
(130), 2-[3-(2-furoyl)-2,5-dimethylpyrrol-1-yl]-2-methylethanol,
(200), 2-(3-benzoyl-2,5-dimethylpyrrol-1-yl)ethyl methyl ether,
(202), 2-(3-benzoyl-2,5-dimethylpyrrol-1-yl)-1-methylethyl methyl ether.
(204), 2-(3-benzoyl-2,5-dimethylpyrrol-1-yl)-1-ethylethyl methyl ether,
(206), 2-(3-benzoyl-2,5-dimethylpyrrol-1-yl)-2-methylethyl methyl ether,
(208), (2S)-2-(3-benzoyl-2,5-dimethylpyrrol-1-yl)-2-methylethyl methyl ether, (210), (2R)-2-(3-benzoyl-2,5-dimethylpyrrol-1-yl)-2-methylethyl methyl ether,
(212), 2-(3-benzoyl-2,5-dimethylpyrrol-1-yl)-2-ethylethyl methyl ether,
(214), 2-(3-benzoyl-2,5-dimethylpyrrol-1-yl)-2-isopropylethyl methyl ether,
(216), 2-(3-benzoyl-2,5-dimethylpyrrol-1-yl)-2-isobutylethyl methyl ether,
(218), 2-(3-benzoyl-2,5-dimethylpyrrol-1-yl)-2-methyl-1-phenylethyl methyl ether,
(220), 2-(3-benzoyl-2,5-dimethylpyrrol-1-yl)-2-methylethyl ethyl ether,
(222), 2-(3-benzoyl-2,5-dimethylpyrrol-1-yl)-2-methylethyl isopropyl ether,
(224), 2-(3-benzoyl-2,5-dimethylpyrrol-1-yl)-2-methylethyl n-butyl ether,
(226), 2-(3-benzoyl-2,5-dimethylpyrrol-1-yl)ethyl phenyl ether,
(228), 2-(3-benzoyl-2,5-dimethylpyrrol-1-yl)-2-methylethyl phenyl ether,
(230), 2-(3-isobutyryl-2,5-dimethylpyrrol-1-yl)-ethyl methyl ether,
(232), 2-(3-pivaloyl-2,5-dimethylpyrrol-1-yl)-ethyl methyl ether,
(234), 2-(3-cyclohexylcarbonyl-2,5-dimethylpyrrol-1-yl) ethyl methyl ether,
(236), 2-(3-cyclohexylcarbonyl-2,5-dimethylpyrrol-1-yl)-2-methylethyl methyl ether,
(238), 2-(3-o-methylbenzoyl-2,5-dimethylpyrrol-1-yl) ethyl methyl ether,
(240), 2-(3-o-methylbenzoyl-2,5-dimethylpyrrol-1-yl)-2-methylethyl ethyl ether,
(242), 2-(3-m-chlorobenzoyl-2,5-dimethylpyrrol-1-yl)-ethyl methyl ether,
(244), 2-(3-p-methoxybenzoyl-2,5-dimethylpyrrol-1-yl) ethyl methyl ether,
(246), 2-(3-o-acetoxybenzoyl-2,5-dimethylpyrrol-1-yl)-2-methylethyl methyl ether,
(248), 2-(3-o-hydroxybenzoyl-2,5-dimethylpyrrol-1-yl)-2-methylethyl methyl ether,
(250), 2-[3-(2-furoyl)-2,5-dimethylpyrrol-1-yl]-ethyl methyl ether,
(252), 2-[3-(2-thenoyl)-2,5-dimethylpyrrol-1-yl]-ethyl methyl ether,
(254), 2-[3-(2-thenoyl)-2,5-dimethylpyrrol-1-yl]-2-methylethyl methyl ether,
(256), 2-[3-(3-thenoyl)-2,5-dimethylpyrrol-1-yl]-2-methylethyl ethyl ether,
(258), 2-[3-(2-thenoyl)-2,5-dimethylpyrrol-1-yl]-2-methyl-1-phenylethyl methyl ether,
(260), 2-(3-nicotinoyl-2,5-dimethylpyrrol-1-yl)-ethyl methyl ether,
(262), 2-[3-(2-pyridinecarbonyl)-2,5-dimethylpyrrol-1-yl]-2-methylethyl methyl ether,
(264), 2-(3-isonicotinoyl-2,5-dimethylpyrrol-1-yl)-2-methylethyl ethyl ether,
(266), 2-[3-(1-cyclohexenylcarbonyl)-2,5-dimethylpyrrol-1-yl]-2-methylethyl methyl ether,
(268), 2-(3-cyclopentylcarbonyl-2,5-dimethylpyrrol-1-yl)-2-methylethyl methyl ether,
(270), 2-[3-(1-cyclopentenylcarboxyl)-2,5-dimethylpyrrol-1-yl]-2-methylethyl methyl ether,
(272), 2-(3-benzoyl-2,5-dimethylpyrrol-1-yl)ethyl benzyl ether,
(274), 2-(3-n-hydroxybenzoyl-2,5-dimethylpyrrol-1-yl)-2-methylethyl methyl ether,
(276), 2-(3-p-hydroxybenzoyl-2,5-dimethylpyrrol-1-yl)-2-methylethyl methyl ether,
(278), 2-(3-benzoyl-2,5-dimethylpyrrol-1-yl)-2-methylethyl o-methoxycarbonylphenyl ether,
(280), 2-(3-benzoyl-2,5-dimethylpyrrol-1-yl)-2-methylethyl o-carboxyphenyl ether,
(282), 2-(3-benzoyl-2,5-dimethylpyrrol-1-yl)-2-methylethyl p-carboxyphenyl ether,
(284), 2-(3-benzoyl-2,5-dimethylpyrrol-1-yl)-2-methylethyl n-carboxyphenyl ether,
(286), 2-(3-benzoyl-2,5-dimethylpyrrol-1-yl)-2-methylethyl o-acetoxybenzyl ether,
(288), 2-(3-benzoyl-2,5-dimethylpyrrol-1-yl)-2-methylethyl o-hydroxybenzyl ether,
(290), 2-(3-benzoyl-2,5-dimethylpyrrol-1-yl)-2-methylethyl p-hydroxybenzyl ether,
(292), 2-(3-benzoyl-2,5-dimethylpyrrol-1-yl)-2-methylethyl m-hydroxybenzyl ether,
(294), 2-(3-benzoyl-2,5-dimethylpyrrol-1-yl)-2-methyl-1-p-hydroxyphenylethyl methyl ether,
(2) Pyrrole derivatives having an acyloxy group of formula (I-1b) as a substituent:-
(300), 2-(3-benzoyl-2,5-dimethylpyrrol-1-yl)-ethyl acetate,
(302), 2-(3-benzoyl-2,5-dimethylpyrrol-1-yl)-1-methyl acetate,
(304), 2-(3-benzoyl-2,5-dimethylpyrrol-1-yl)-1-ethylethyl acetate,
(306), 2-(3-benzoyl-2,5-dimethylpyrrol-1-yl)-2-methylethyl acetate,
(308), 2-(3-benzoyl-2,5-dimethylpyrrol-1-yl)-2-methylethyl acetate,
(310), 2-(3-benzoyl-2,5-dimethylpyrrol-1-yl)-2-methylethyl valerate,
(312), 2-(3-benzoyl-2,5-dimethylpyrrol-1-yl)-2-methylethyl decanoate,
(314), 2-(3-benzoyl-2,5-dimethylpyrrol-1-yl)-2-methylethyl benzoate,
(316), (2S)-2-(3-benzoyl-2,5-dimethylpyrrol-1-yl)-2-methylethyl acetate,
(318), (2R)-2-(3-benzoyl-2,5-dimethylpyrrol-1-yl)-2-methylethyl acetate,
(320), 2-(3-benzoyl-2,5-dimethylpyrrol-1-yl)-2-ethylethyl acetate,
(322), 2-(3-benzoyl-2,5-dimethylpyrrol-1-yl)-2-ethylethyl benzoate,
(324), 2-(3-benzoyl-2,5-dimethylpyrrol-1-yl)-2-isopropylethyl acetate,
(326), 2-(3-benzoyl-2,5-dimethylpyrrol-1-yl)-2-isobutylethyl acetate,
(328), 2-(3-benzoyl-2,5-dimethylpyrrol-1-yl)-2-methyl-1-phenylethyl acetate,
(330), 2-(3-o-chlorobenzoyl-2,5-dimethylpyrrol-1-yl)-2-methylethyl acetate,
(332), 2-(3-o-hydroxybenzoyl-2,5-dimethylpyrrol-1-yl)-2-methylethyl acetate,
(334), (2-(3-o-acetoxybenzoyl-2,5-dimethylpyrrol-1-yl)-2-methylethyl acetate,
(336), 2-[3-(2-thenoyl)-2,5-dimethylpyrrol-1-yl]-2-methylethyl acetate,
(338), 2-(3-cyclohexylcarbonyl-2,5-dimethylpyrrol-1-yl)-2-methylethyl acetate,
(340), 2-(3-p-chlorobenzoyl-2,5-dimethylpyrrol-1-yl) ethyl acetate.
(3) Pyrrole derivatives of formula (I-1c) having a sulfide, sulfinyl or sulfonyl group as a substituent:
(400), 2-(3-benzoyl-2,5-dimethylpyrrol-1-yl)ethyl methyl sulfide,
(402), 2-(3-benzoyl-2,5-dimethylpyrrol-1-yl)-2-methylethyl methyl sulfide, (404), 2-(3-benzoyl-2,5-dimethylpyrrol-1-yl)ethyl phenyl sulfide,
(406), 2-(3-benzoyl-2,5-dimethylpyrrol-1-yl)-2-methylethyl phenyl sulfide,
(408), 2-(3-benzoyl-2,5-dimethylpyrrol-1-yl)-2-methylethyl methyl sulfoxide,
(410), 2-(3-benzoyl-2,5-dimethylpyrrol-1-yl)ethyl phenyl sulfoxide,
(412), 2-(3-benzoyl-2,5-dimethylpyrrol-1-yl)-2-methylethyl phenyl sulfoxide,
(414), 2-(3-benzoyl-2,5-dimethylpyrrol-1-yl)-2-methylethyl phenyl sulfone.

(4) Pyrrole derivatives of formula (I-2a) having a formyl group as a substituent:
(500), 3-benzoyl-2,5-dimethylpyrrol-1-yl acetaldehyde,
(502), 2-(3-benzoyl-2,5-dimethylpyrrol-1-yl)-propionaldehyde,
(504), 2-(3-benzoyl-2,5-dimethylpyrrol-1-yl)-butyraldehyde,
(506), 2-[3-(2-thenoyl)-2,5-dimethylpyrrol-1-yl]propionaldehyde.

(5) Pyrrole derivatives of formula (I-2b) having an acyl group as a substituent:
(600), 1-(3-benzoyl-2,5-dimethylpyrrol-1-yl)-2-propanone,
(602), 2-(3-benzoyl-2,5-dimethylpyrrol-1-yl)-3-heptanone, (6) Pyrrole derivatives of formula (I-2c) having an acyloxy group as a substituent:
(700), methyl 3-benzoyl-2,5-dimethylpyrrol-1-yl-acetate,
(702), ethyl 3-benzoyl-2,5-dimethylpyrrol-1-yl-acetate,
(704), methyl 2-(3-benzoyl-2,5-dimethylpyrrol-1-yl)propionate,
(706), ethyl 2-(3-benzoyl-2,5-dimethylpyrrol-1-yl) propionate,
(708), n-butyl 2-(3-benzoyl-2,5-dimethylpyrrol-1-yl) propionate,
(710), phenyl 2-(3-benzoyl-2,5-dimethylpyrrol-1-yl) propionate,
(712), p-chlorophenyl 2-(3-benzoyl-2,5-dimethylpyrrol-1-yl)propionate,
(714), o-hydroxyphenyl 2-(3-benzoyl-2,5-dimethylpyrrol-1-yl)propionate,
(716), p-methylphenyl 2-(3-benzoyl-2,5-dimethylpyrrol-1-yl)propionate,
(718), 2,6-dichlorophenyl 2-(3-benzoyl-2,5-dimethylpyrrol-1-yl)propionate,
(720), benzyl 2-(3-benzoyl-2,5-dimethylpyrrol-1-yl) propionate,
(722), o-methoxybenzyl 2-(3-benzoyl-2,5-dimethylpyrrol-1-yl)propionate,
(724), p-acetoxybenzyl 2-(3-benzoyl-2,5-dimethylpyrrol-1-yl)propionate,
(726), methyl 2-(3-p-chlorobenzoyl-2,5-dimethylpyrrol-1-yl)propionate,
(728), methyl 2-(3-nicotinoyl-2,5-dimethylpyrrol-1-yl)propionate,
(730), ethyl 3-(2-thenoyl)-2,5-dimethylpyrrol-1-yl acetate,
(732), p-methoxycarbonylphenyl 2-(3-benzoyl-2,5-dimethylpyrrol-1-yl)propionate,
(734), o-carboxyphenyl 2-(3-benzoyl-2,5-dimethylpyrrol-1-yl)propionate,
(736), p-acetoxybenzyl 2-(3-benzoyl-2,5-dimethylpyrrol-1-yl)propionate,
(738), o-hydroxybenzyl 2-(3-benzoyl-2,5-dimethylpyrrol-1-yl)propionate, (7) Pyrrole derivatives of formula (I-2d) having an amido or hydrazido group as a substituent:
(800), 3-benzoyl-2,5-dimethylpyrrol-1-ylacetamide,
(802), 2-(3-benzoyl-2,5-dimethylpyrrol-1-yl)propionamide,
(804), N-methyl-2-(3-benzoyl-2,5-dimethylpyrrol-1-yl)propionamide,
(806), N,N-diethyl-2-(3-benzoyl-2,5-dimethylpyrrol-1-yl)propionamide,
(808), N-phenyl-2-(3-benzoyl-2,5-dimethylpyrrol-1-yl)propionamide,
(810), N,N-bis(2-hydroxyethyl)-2-(3-benzoyl-2,5-dimethylpyrrol-1-yl)propionamide,
(812), 2-(3-benzoyl-2,5-dimethylpyrrol-1-yl)propionylpyrrolidine,
(814), 2-(3-benzoyl-2,5-dimethylpyrrol-1-yl)-propionylpiperidine,
(816), 2-(3-benzoyl-2,5-dimethylpyrrol-1-yl)-propionylmorpholine,
(818), 3-benzoyl-2,5-dimethylpyrrol-1-yl acetohydrazide,
(820), 2-(3-benzoyl-2,5-dimethylpyrrol-1-yl)propiohydrazide,
(822), N'-ethyl-2-(3-benzoyl-2,5-dimethylpyrrol-1-yl) propiohydrazide,
(824), N'-phenyl-2-(3-benzoyl-2,5-dimethylpyrrol-1-yl) propiohydrazide, (8) Pyrrole derivatives of formula (I-2d) having an acetal group as a substituent:
(900), 3-benzoyl-2,5-dimethylpyrrol-1-ylacetoaldehyde dimethyl acetal,
(902), 2-(3-benzoyl-2,5-dimethylpyrrol-1-yl)-propionaldehyde dimethyl acetal,
(904), 2-(3-benzoyl-2,5-dimethylpyrrol-1-yl)-propionaldehyde diethyl acetal,
(906), 2-(3-benzoyl-2,5-dimethylpyrrol-1-yl)-propionaldehyde di-n-butyl acetal,
(908), 3-(3-benzoyl-2,5-dimethylpyrrol-1-yl)-2-butanone diethyl acetal,
(910), 2-(3-benzoyl-2,5-dimethylpyrrol-1-yl)-3-hexanone diethyl acetal,
(912), 2-(3-benzoyl-2,5-dimethylpyrrol-1-yl)-3-heptanone ethylene acetal,
(914), 2-[3-(2thenoyl)-2,5-dimethylpyrrol-1-yl]-propionaldehyde dimethyl acetal.

[PROCESSES FOR PREPARATION]

The 1-substituted-3-acylpyrrole derivatives of formula (I) of this invention can be prepared as follows:

(1) The pyrrole derivatives of formula (I-1a) having an ether group as a substituent, the pyrrole derivatives of formula (I-1b) having an acyloxy group as a substituent, the pyrrole derivatives of formula (I-1c) having a sulfide group as a substituent, the pyrrole derivatives of formula (I-2b) having an acyl group as a substituent, and the pyrrole derivatives of formula (I-2c) having an ester group as a substituent can each be prepared by condensing 1-substituted pyrrole derivatives of the formula

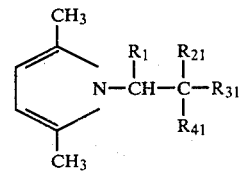 (II)

wherein $R_1$ is as defined in formula (I), and $R_{21}$, $R_{31}$ and $R_{41}$ are as defined in (1) or (2) below, (1) $R_{21}$ represents a group of the formula $-X_1-R_{51}$ in which $X_1$ represents an oxygen or sulfur atom, and $R_{51}$ represents a lower alkyl group containing 1 to 4 carbon atoms, an acyl group containing 2 to 10 carbon atoms, or a phenyl or benzyl group which may be substituted by a hydroxyl group, a carboxyl group, or an alkoxycarbonyl or acyloxy group with 2 to 4 carbon atoms; and $R_{31}$ and $R_{41}$ are the same or different and each represent a hydrogen atom, a lower alkyl group with 1 to 4 carbon atoms, or a phenyl group which may be substituted by a hydroxyl group, a carboxyl group or an alkoxycarbonyl or acyloxy group with 2 to 4 carbon atoms; and (2) $R_{21}$ and $R_{31}$ together represent $=O$, and $R_{41}$ represents a lower alkyl or alkoxy group with 1 to 4 carbon atoms, or a phenoxy or benzyloxy group which may be substituted by 1 or 2 halogen atoms, hydroxyl groups, alkyl or alkoxy groups with 1 to 3 carbon atoms, or acyloxy groups with 2 to 4 carbon atoms, said substituents being the same or different, with an anhydride or a halide of carboxylic acid of the formula

$$\phi-COOH \qquad (III)$$

wherein $\phi$ is as defined in formula (I), in the presence of acid catalysts.

Examples of preferred acid catalysts are Lewis acids such as $BF_3$, $AlCl_3$ or $SnCl_4$ or Brønstedt acids such as HI. When HI is used as an acid catalyst, the use of an acid anhydride is preferred. In this case, the desired 1-substituted-3-acylpyrrole derivative can be obtained in a high yield, and a by-product 1-substituted-3,4-diacylpyrrole derivative does not form. Accordingly, such a process is believed to be superior.

(2) The pyrrole derivatives of formula (I-1a) having an alcoholic hydroxyl group as a substituent can be prepared by hydrolyzing the pyrrole derivatives of formula (I-1b) having an acyloxy group as a substituent in a customary manner.

(3) The pyrrole derivatives of formula (I-1c) having a sulfinyl or sulfonyl group as a substituent can be prepared by oxidizing the pyrrole derivatives of formula (I-1c) having a sulfide group as a substituent under ordinary conditions for oxidizing the sulfide bond.

(4) The pyrrole derivatives of formula (I-2a) having a formyl group as a substituent can be prepared by partially oxidizing the pyrrole derivatives of formula (I-1a) having an alcoholic hydroxyl group as a substituent under ordinary conditions.

(5) The pyrrole derivatives of formula (I-2d) having an amido or hydrazido group as a substituent can be prepared by hydrolyzing the pyrrole derivatives of formula (I-2c) having an ester group as a substituent in a customary manner to form pyrrole derivatives having the corresponding carboxyl group as a substituent, reacting the resulting pyrrole derivatives, either as such or after having been converted to active derivatives, in the presence of condensing agents, and amidating the products with ammonia, amines or hydrazine.

(6) The pyrrole derivatives of formula (I-3) having an acetal group as a substituent can be prepared by converting the formyl group or acyl group of the pyrrole derivatives of formula (I-2a) or (I-2b) into the acetal group by an ordinary method.

Accordingly, the process for preparing the 1-substituted-3-acylpyrrole derivative of formula (I) in accordance with this invention comprises condensing the 1-substituted pyrrole derivative of formula (II) with an anhydride or a halide of a carboxylic acid of formula (III) in the presence of an acid catalyst, and then if desired, hydrolyzing, oxidizing or amidating the resulting product in a manner known per se.

The processes of the invention are described in more details below.

(1) CONDENSATION REACTION BETWEEN THE 1-SUBSTITUTED PYRROLE DERIVATIVE OF FORMULA (II) AND THE ANHYDRIDE OR HALIDE OF CARBOXYLIC ACID OF FORMULA (III)

This condensation reaction is generally known as a Friedel-Crafts reaction, and can be performed, for example in accordance with the methods described in detail in G. A. Olah, "Friedel-Crafts and Related Reactions", and "Organic Reactions", Vol. 2, p. 130 (1944), ibid. Vol. 3, p. 1 (1946), and ibid. Vol. 5, p. 229 (1949).

When the acid halide or acid anhydride is used an acylating agent, Lewis acids such as aluminum chloride, aluminum bromide, boron trifluoride, titanium tetrachloride, tin tetrachloride or zinc chloride, and Brønstedt acids such as hydriodic acid can be suitably used as the acid catalyst. Of these, aluminum chloride and hydriodic acid are preferred.

The reaction proceeds in the absence of a solvent, but to have the reaction proceed more smoothly, an organic medium may be used.

Inert organic solvents usually employed in the Friedel-Crafts reaction can be used as such organic media. Specific examples include carbon tetrachloride, haloalkanes such as dichloromethane, dichloroethane and tetrachloroethane, nitromethane, aromatic hydrocarbons such as benzene, toluene, xylene or nitrobenzene, and carbon disulfide.

The amount of the acylating agent derived from the carboxylic acid of formula (III) used in this invention is 0.5 to 5 moles, preferably 0.8 to 2.5 moles, per mole of the starting pyrrole derivatives of formula (II). The amount of the acid catalyst is 0.5 to 5 moles, preferably 0.8 to 2.5 moles, per mole of the starting pyrrole derivative of formula (II). The amount of the inert organic solvent is the one sufficient to have the reaction proceed smoothly. Usually, it is 1 to 100 times, preferably 2 to 20 times, the volume of the starting material.

The reaction temperature is in the range of from minus 78° C. to plus 200° C. When hydriodic acid is used as an acid catalyst, the reaction temperature is preferably 50° to 180° C., especially preferably 80° to 150° C. When a Lewis acid is used as the acid catalyst, the reaction temperature is preferably $-30°$ C. to 150° C., more preferably $-10°$ C. to 80° C.

The end point of the reaction can be determined by tracing it by gas chromatography or thin-layer chromatography. The reaction time, which differs according to the reaction temperature and the types of the acylating agent and the medium, is about 30 minutes to 5 hours at room temperature.

After the reaction, the desired 1-substituted-3-acylated pyrrole derivatives is isolated in the following manner. After optionally distilling off the solvent, the reaction mixture is treated with an acid such as dilute hydrochloric acid (when a Lewis acid is used) or an alkali such as sodium hydroxide or sodium bicarbonate (when hydriodic acid is used). The treated mixture is extracted with an extracting solvent such as diethyl ether, benzene, hexane, ethyl acetate, dichloromethane or chloroform. The resulting organic layer is washed with water, an aqueous solution of sodium hydrogen carbonate, an aqueous solution of sodium chloride, etc., then dried, and concentrated to afford a crude product. The crude product is separated by a purifying procedure such as column chromatography, thin-layer chromatography, distillation or recrystallization. Thus, the acylated pyrrole derivative can be isolated in pure form.

The 1-substituted pyrrole derivative of formula (II) used in the condensation reaction can be prepared as shown in Referential Examples to be given hereinbelow.

The basic reaction is a dehydrocondensation reaction between the corresponding 1,4-diketone and an optically active or inactive α-amino acid or its ester, or a dehydrocondensation reaction between the corresponding 1,4-diketone and an optically active or inactive β-aminoethanol. The resulting product can be used directly as the starting material of formula (II). If desired, it may be subjected to known reactions such as reduction, hydrolysis or etherification to form raw materials within the definition of formula (II). This basic reaction is known as a pyrrole synthesis method of Paal-Knorr and is described in detail, for example, in Merck Index, 8th Edition, p. 1197 (1968), or Wagner and Zook, "Synthetic Organic Chemistry", p. 840 (1953).

The anhydride or halide of the aromatic carboxylic acid of formula (III), the other starting material, is an acylating agent known per se. Examples of the carboxylic acid of formula (III) are benzoic acid, o-methylbenzoic acid, m-methylbenzoic acid, p-methylbenzoic acid, p-acetoxybenzoic acid, o-hydroxybenzoic acid, m-hydroxybenzoic acid, p-chlorobenzoic acid, p-bromobenzoic acid, p-fluorobenzoic acid, p-methoxybenzoic acid, cyclohexanecarboxylic acid, cyclohexene-1-carboxylic acid, 2-furanecarboxylic acid, 3-furanecarboxylic acid, 2-thiophenecarboxylic acid, 2-thiophenecarboxylic acid, picolic acid, nicotinic acid, and isonicotinic acid.

The acid halides are, for example, the fluorides, chlorides, bromides and iodides of these acids. Usually, the acid chlorides and acid bromides are used conveniently. The acid anhydrides are, for example, those resulting from the dehydration-condensation of two molecules of the corresponding aromatic carboxylic acids, but mixed acid anhydrides derived from different carboxylic acids can also be used.

When hydriodic acid is used as an acid catalyst for the condensation reaction, the acid anhydrides are preferred.

As will be described in detail hereinbelow, those 1-substituted-3-acylpyrrole derivatives of the invention which have an ether group as a substituent have especially superior pharmacological activities. These compounds can also be prepared conveniently by subjecting the 1-substituted-3-acylpyrrole derivatives of the invention having the above formula (I-1a) which have an alcoholic hydroxyl group to a reaction generally known as the Williamson's ether synthesis, namely a reaction in the presence of an alkyl halide such as methyl iodide or ethyl iodide and an alkali metal hydride such as sodium hydride.

Specific conditions for the reaction are described in Referential Example 3 and some Examples given hereinbelow.

The 1-substituted-3-acylpyrrole derivatives of formula (I-1b) having an acyloxy group and the 1-substituted-3-acylpyrrole derivatives of formula (I-2b) having an acyl group can be converted to those having a different acyloxy or acyl group by hydrolyzing them to remove the acyl groups, and reacting the products with other carboxylic acid anhydride or halides.

(2) PRODUCTION OF PYRROLE DERIVATIVES OF FORMULA (I-1a) HAVING AN ALCOHOLIC HYDROXYL GROUP AS A SUBSTITUENT BY THE HYDROLYSIS OF PYRROLE DERIVATIVES OF FORMULA (I-1b) HAVING AN ACYLOXY GROUP AS A SUBSTITUENT:

This hydrolysis reaction is a known hydrolysis of ester groups. Generally, it is carried out by treating the starting compounds at 0° to 80° C. in the presence of an alkali such as sodium hydroxide or potassium hydroxide or a mineral acid such as hydrochloric acid, preferably the alkali, in an alcohol such as methanol or ethanol in the copresence, if desired, of an ether solvent such as tetrahydrofuran or dioxane.

(3) PREPARATION OF PYRROLE DERIVATIVES OF FORMULA (I-1c) HAVING A SULFINYL OR SULFONYL GROUP BY OXIDATION OF PYRROLE DERIVATIVES OF FORMULA (I-1c) HAVING A SULFIDE GROUP AS A SUBSTITUENT:

This oxidation reaction is known per se as a sulfide bond oxidizing reaction.

For example, sodium metaperiodate or m-chloroperbenzoic acid is frequently used as an oxidizer. When sodium metaperiodate ($NaIO_4$) is used, 1-substituted-3-acylpyrrole derivatives having a sulfinyl group are easy to obtain. Known reaction conditions are applicable to the reaction solvent, the reaction temperature, etc.

(4) PREPARATION OF PYRROLE DERIVATIVES OF FORMULA (I-2a) HAVING A FORMYL GROUP AS A SUBSTITUENT BY THE PARTIAL OXIDATION OF PYRROLE DERIVATIVES OF FORMULA (I-1a) HAVING AN ALCOHOLIC HYDROXYL GROUP AS A SUBSTITUENT:

This partial oxidation reaction is well known per se as the synthesis of aldehydes by partial oxidation of alcohols.

The oxidation reaction easily proceeds by using dimethylsulfoxide, for example, as an oxidizer in a halogenated hydrocarbon solvent such as methylene chloride in the presence of oxallyl chloride and a tertiary amine such as triethylamine.

A reaction involving the use of a complex of chromic anhydride and pyridine can also be applied equally.

Other oxidizing methods can be applied as desired.

(5) PREPARATION OF PYRROLE DERIVATIVES OF FORMULA (I-2d) HAVING AN AMIDO OR HYDRAZIDO GROUP FROM PYRROLE DERIVATIVES OF FORMULA (I-2c) HAVING AN ESTER GROUP:

This can be performed by hydrolyzing the ester group in the same way as in method (2) to form a pyrrole derivative having a carboxyl group, and converting it to an amide or hydrazide by a reaction known per se.

This amide- or hydrazide-forming reaction is carried out, for example, by reacting the pyrrole derivative containing a carboxyl group with a chloroformate such as ethyl chloroformate or isobutyl chloroformate in the presence of an amine to form a mixed acid anhydride, and treating the product with ammonia, an amine or hydrazide.

This reaction can also be effected by reacting the pyrrole derivative containing a carboxyl group directly with ammonia or the like in the presence of a dehydrocondensing agent such as dicyclohexyl carbodiimide.

(6) PREPARATION OF PYRROLE DERIVATIVES OF FORMULA (I-3) HAVING AN ACETAL GROUP AS A SUBSTITUENT FROM PYRROLE DERIVATIVES OF FORMULA (I-2a) OR (I-2b) HAVING A FORMYL OR ACYL GROUP AS A SUBSTITUENT:

This acetal-forming reaction is well known, and is carried out, for example, by heating with an alcohol or glycol such as methanol, ethanol or ethylene glycol, or with ethyl orthoformate in the presence of a protonic acid such as sulfuric acid or p-toluenesulfonic acid.

[PHARMACOLOGICAL ACTIVITIES AND DRUG FORMULATIONS]

The 1-substituted-3-acylpyrrole derivatives of general formula [I] of this invention generally have a superior activity of inhibiting platelet aggregation, and a low antiinflammatory (carrageenan edema inhibiting) activity, and are specific in exhibiting this characteristic biological response.

Accordingly, these compounds are administered to mammals including man when it is desired to inhibit platelet aggregation and to inhibit or prevent thrombus formation. Thus, these compounds are useful for various prophylactic and therapeutic purposes such as the prevention of cardiovascular infractions and post-operative thrombosis, the promotion of patency of vascular prostheses after surgical operation, and the prevention and treatment of atherosclerosis, arteriosclerosis, etc.

They are also used to prevent onset of cerebral ischemia in patients of senile diseases, and to prevent or treat myocardial infraction and poplexy for a long period of time after their seizure.

For these purposes, the compounds of this invention can be administered perorally, intrarectally, or parenterally (e.g., subcutaneously, intramuscularly). Preferably, they are administered orally or intrarectally, and this is convenient for patients.

For peroral administration, the compounds of the invention are formulated into solid or liquid preparations. Solid preparations include tablets, pills, powders and granules. In such solid preparations, at least one active compound is mixed with at least one inert diluent such as calcium carbonate, potato starch, alginic acid or lactose. Other additives such as lubricants (e.g., magnesium stearate) may also be included. Drug formulation is performed in a customary manner.

Liquid preparations for oral administration include emulsions, solutions, suspensions, syrups and elixirs and a general pharmaceutically acceptable inert diluent such as water or liquid paraffin. In addition to the inert diluent, these pharmaceutical preparations contain auxiliary agents such as wetting agents, suspending aids, sweetenings, flavoring agents, perfumes or antiseptics.

The liquid preparations may be encapsulated in absorbable materials such as gelatin.

Solid preparations for intrarectal administration include suppositories containing at least one active compound and prepared by a method known per se.

Preparations for parenteral administration are aseptic aqueous or non-aqueous solutions, suspensions or emulsions. Non-aqueous solutions or suspensions contain propylene glycol, polyethylene glycol, vegetable oils such as olive oil, and injectable organic esters such as ethyl oleate, etc. These preparations can also include auxiliary agents such as antiseptics, wetting agents, emulsifiers and dispersing agents. These preparations can be sterilized, for example, by filtration through a bacterium-holding filter, mixing of a bactericide, or by irradiation. Alternatively, aseptic solid preparations are first produced, and immediately prior to use, dissolved in aseptic water or an aseptic solvent for injection.

The dosage of the 1-substituted-3-acylpyrrole derivative, an active compound in accordance with this invention, is about 0.005 to about 200 mg, preferably 0.01 to 100 mg, per day per kilogram of body weight. The dosage, of course, depends upon the condition, body weight and age of a patient, and the route of administration.

As stated hereinabove, the novel 1-substituted-3-acylpyrrole derivatives provided by this invention exhibit very specific pharmacological activities in that they have a superior activity of inhibiting platelet aggregation and a low antiinflammatory activity.

The following Referential Examples and Examples illustrate the present invention more specifically.

REFERENTIAL EXAMPLE 1

Alanine ethyl ester hydrochloride (30.8g; 0.2 mole) was dissolved in 100 ml of acetic acid. Acetonylacetone (22.8 g; 0.2 mole) and then 16.4 g (0.2 mole) of sodium acetate were added to the solution, and the mixture heated under reflux for 5 hours. The acetic acid was distilled off under reduced pressure, and ethyl acetate added to the residue. The organic layer was washed with an aqueous solution of sodium hydrogen carbonate, dried over anhydrous magnesium sulfate, and concentrated under reduced pressure to afford 29.2 g of a crude product. The product was chromatographed on a column of silica gel using cyclohexane/ethyl acetate (4/1) as an eluent to afford ethyl 2-(2,5-dimethylpyrrol-1-yl)propionate (23.0 g, 0.118 mole, 59.0%).

IR (neat): 3100, 3000, 2950, 1750, 1640, 1585, 1520, 1445, 1405, 1320, 1300, 1220, 1120, 1075, 1050, 1020, 980, 860 and 755 cm$^{-1}$.

NMR (CO14, δ (ppm)): 1.16 (3H, t, J=7H$_z$, CH$_3$ of the ethyl group), 1.50 (3H, d, J=7Hz, CH-$\underline{CH_3}$), 2.08 (6H, s, CH$_3$ on the pyrrole ring), 4.10 (2H, q, J=7Hz, methylene of the ethyl group), 4.67 (1H, q, J=7Hz, $\underline{CH}$-CH$_3$), 5.55 (2H, s, H on the pyrrole ring).

In the same way as above, methyl 2-(2,5-dimethylpyrrol-1-yl)propionate and ethyl 2,5-dimethylpyrrol-1-yl-acetate were synthesized.

REFERENTIAL EXAMPLE 2

Lithium aluminum hydride (3.1 g; 80.5 mmoles) was added to 100 ml of dry ether, and an ether solution (50 ml) of 17.9 g (91.8 mmoles) of ethyl 2-(2,5-dimethylpyrrol-1-yl)propionate was gradually added dropwise to the mixture. After the addition, the mixture was heated under reflux for 2 hours, and worked up with a saturated aqueous solution of sodium sulfate. The ethereal layer was concentrated under reduced pressure to afford 13.5 g of crude 2-(2,5-dimethylpyrrol-1-yl)-1-propanol. Acetic anhydride (50 ml) and 50 ml of pyridine were added to the product, and the mixture was allowed to stand at room temperature for 20 hours. It was then concentrated under reduced pressure and then distilled under reduced pressure to afford 2-(2,5-dimethylpyrrol-1-yl)propyl acetate (13.0 g, 66.8 mmoles, 75.7%) having a boiling point of 116°–118° C./6 mmHg.

IR (neat): 3090, 2970, 2940, 1745, 1515, 1445, 1395, 1380, 1365, 1330, 1295, 1230, 1040, 1020, 985, 900, 835, 750, 695 cm$^{-1}$.

NMR(CCl$_4$, δ (ppm)): 1.42 (3H, d, J=7Hz, CH-CH$_3$), 1.87 (3H, s, OCOCH$_3$), 2.15 (6H, s, CH$_3$ on the pyrrole ring), 4.05–4.70 (3H, m, NCHCH$_2$O), 5.50 (2H, s, H on the pyrrole ring).

In the same way as above, (2S)- and (2R)-2-(2,5-dimethylpyrrol-1-yl)propyl acetate, 2-(2,5-dimethylpyrrole-1-yl)ethyl acetate, 2-(2,5-dimethylpyrrol-1-yl)-2-methyl-1-phenylethyl acetate, and 2-(2,5-dimethylpyrrol-1-yl)-2-isobutylethyl acetate were synthesized.

REFERENTIAL EXAMPLE 3

Sodium hydride (50% content: 6.0 g, 0.12 mmole) was washed with petroleum ether and after removing mineral oil, 100 ml of dimethoxyethane was added. A solution of 15.3 g (0.1 mole) of 2-(2,5-dimethylpyrrol-1-yl)-1-propanol obtained in Referential Example 2 in 50 ml of dimethoxyethane was added gradually to the mixture. The mixture was stirred for 1 hour at room temperature, and 6.6 ml (15.1 g; 0.36 mole) of methyl iodide was added, followed by stirring at room temperature for 20 hours. The solvent was distilled off under reduced pressure, and the residue was chromatographed on a column of silica gel using cyclohexane/ethyl acetate (4/1) as an eluent to afford 2-(2,5-dimethylpyrrol-1-yl)-1-methoxypropane (14.36 g, 0.08 mole, 86.0%).

IR (neat): 3110, 3000, 2950, 2910, 2850, 2750, 1520, 1400, 1330, 1300, 1240, 1200, 1145, 1110, 1020, 1010, 980, 970, 750 cm$^{-1}$.

NMR (CDCl$_3$, δ (ppm)): 1.40 (3H, d, J=7Hz, CH-CH$_3$), 2.16 (6H, s, CH$_3$ on the pyrrole ring), 3.21 (3H, s, OCH$_3$), 3.48 (2H, d, J=7Hz, -CHCH$_2$O-), 4.27 (1H, sextet, J=7Hz, NCHCH$_3$), 5.43 (2H, s. H on the pyrrole ring).

REFERENTIAL EXAMPLE 4

Phenylthioethylamine (5.00 g, 32.68 mmoles) prepared by reacting thiophenol and β-bromoethylamine hydrobromide in the presence of triethylamine and 3.74 g (32.68 mmoles) of acetonylacetone were heated under reflux for 4 hours in 80 ml of acetic acid. The acetic acid was distilled off under reduced pressure, and toluene was added to the residue. The mixture was distilled under reduced pressure. The resulting crude product was chromatographed on a column of silica gel using hexane/benzene as an eluent to afford 2,5-dimethylpyrrol-1-yl-ethyl phenyl sulfide (5.32 g, 22.88 mmoles, 70%).

NMR (CDCl$_3$, δ (ppm)): 2.08 (6H, s, CH$_3$ on the pyrrole ring), 2.82–3.16 (2H, m, —CH$_2$S—), 3.71–4.05 (2H, m, —CH$_2$N—), 5.71 (2H, s, H on the pyrrole ring), 7.1–7.5 (5H, m, Ph).

In the same way as above, 2,5-dimethylpyrrol-1-ylethyl methyl sulfide was obtained.

REFERENTIAL EXAMPLE 5

To a solution of dimethylsulfoxide (1.56 g, 20.0 mmoles) and oxalyl chloride (1.9 g, 15.0 mmoles) in 20 ml of methylene chloride cooled to −78° C. was added 1.67 g (10.0 mmoles) of 3-(2,5-dimethylpyrrol-1-yl)-2-butanol obtained by dehydration cyclization of 3-amino-2-butanol and acetonylacetone in acetic acid. One hour later, 3 ml of triethylamine was added, and the mixture stirred at room temperature for 5 hours. The mixture was extracted with chloroform. The chloroform layer was dried over anhydrous magnesium sulfate, and concentrated, and chromatographed on a column of silica gel using cyclohexane/ethyl acetate (4/1) as an eluent to afford 3-(2,5-dimethylpyrrol-1-yl)-2-butanone (990 mg, 6.0 mmoles, 60%).

NMR (CDCl$_3$, δ (ppm)): 1.53 (3H, d, J=7 Hz, CH-CH$_3$), 2.10 (3H, s, COCH$_3$), 2.08 (6H, s, CH$_3$ on the pyrrole ring), 4.70 (1H, q, NCHCO), 5.57 (2H, s, H on the pyrrole ring).

In the same way as above, 2-(2,5-dimethylpyrrol-1-yl)-3-heptanone was synthesized.

EXAMPLE 1

Synthesis of 2-(3-benzoyl-2,5-dimethylpyrrol-1-yl)-2-methylethanol (106):

In 10 ml of methanol was dissolved 1.24 g (4.15 mmoles) of 2-(3-benzoyl-2,5-dimethylpyrrol-1-yl)-2-methylethyl acetate. Tetrahydrofuran (30 ml) and then 10 ml (10.0 mmoles) of an 1.0 N aqueous solution of sodium hydroxide was added. The mixture was stirred for 3 hours at room temperature. The solvent was distilled off under reduced pressure. The residue was extracted with 50 ml of ethyl acetate three times, and the resulting extracts were dried over anhydrous magnesium sulfate, and concentrated to afford 900 mg of a crude product. The crude product was chromatographed on a column of silica gel using cyclohexane/ethyl acetate (1/1) as an eluent to afford compound (106) (790 mg, 3.07 mmoles, 74.1%).

IR (neat): 3420, 2990, 2940, 2890, 1740, 1625, 1570, 1515, 1450, 1410, 1380, 1340, 1310, 1280, 1240, 1180, 1150, 1060, 1030, 950, 910, 740, 720, 695 cm$^{-1}$.

NMR (CDCl$_3$, δ (ppm)): 1.41 (3H, d, J=7 Hz,

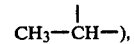

2.17 (3H, s, CH$_3$ at the 5-position of the pyrrole ring), 2.55 (3H, s, CH$_3$ at the 2-position of the pyrrole ring), 3.5–3.9 (3H, m, —CH$_2$OH), 4.31 (1H, m,

5.97 (1H, s, H at the 4-position of the pyrrole ring), 7.23–7.50 and 7.57–7.80 (3H and 2H, m, H on the benzone ring).

Mass spectrum (70 eV; m/e, %): 258 (M+1, 10), 257 (M$^+$, 60), 256 (M-1, 20), 242 (3), 240 (2), 226 (7), 200 (9), 199 (54), 198 (30), 180 (10), 122 (28), 121 (8), 120 (7), 106 (9), 105 (100), 77 (39), 67 (5), 63 (3), 53 (7), 51 (9), 42 (10).

EXAMPLE 2

Synthesis of (2S)-2-(3-benzoyl-2,5-dimethylpyrrol-1-yl)-2-methylethanol (108):

In the same way as in Example 1, compound (108) was prepared in a yield of 61.9% from (2S)-2-(3-benzoyl-2,5-dimethylpyrrol-1-yl)-2-methylethyl acetate ($[\alpha]_D^{21} = +11.7°$, c=0.0174, $C_2H_5OH$).

IR (neat): 3400, 3050, 2980, 2930, 1740, 1630, 1620, 1605, 1570, 1515, 1445, 1420, 1375, 1315, 1295, 1250, 1190, 1175, 1160, 1100, 1060, 1035, 1000, 930, 910, 850, 810, 790, 775, 730, 695 cm$^{-1}$.

NMR (CDCl$_3$, δ(ppm)): 1.37 (3H, d, J=6 Hz, CH-C$\underline{H}_3$), 2.13 (3H, s, CH$_3$ at the 5-position of the pyrrole ring), 2.51 (3H, s, CH$_3$ at the 2-position of the pyrrole ring), 3.77 (2H, bd, J=6 Hz, CHC$\underline{H}_2$OH), 3.83 (1H, bs, OH), 4.32 (1H, m, CH$_3$C$\underline{H}$CH$_2$), 5.93 (1H, s, H at the 4-position of the pyrrole ring), 7.20–7.50 (3H, m, H on the benzene ring (to be referred to as Ph)), 7.50–7.80 (2H, m, H on Ph).

$[\alpha]_D^{21} = +15.3°$ (c=0.0506, $C_2H_5OH$).

EXAMPLE 3

Synthesis of (2R)-2-(3-benzoyl-2,5-dimethylpyrrol-1-yl)-2-methylethanol (110):

In the same way as in EXample 1, compound (110) was prepared in a yield of 54.3% from (2R)-2-(3-benzoyl-2,5-dimethylpyrrol-1yl)-2-methylethyl acetate ($[\alpha]_D^{21} = -13.7°$, c=0.0182, $C_2H_5OH$).

IR (neat): 3420, 3060, 2990, 2950, 1740, 1630, 1620, 1605, 1570, 1515, 1450, 1420, 1375, 1320, 1300, 1250, 1190, 1180, 1160, 1105, 1065, 1035, 1000, 930, 910, 850, 810, 790, 775, 730, 700 cm$^{-1}$.

NMR (CDCl$_3$, δ(ppm)): 1.37 (3H, d, J=7 Hz, CH-C$\underline{H}_3$), 2.13 (3H, s, CH$_3$ at the 5-position of the pyrrole ring), 2.51 (3H, s, CH$_3$ at the 2-position of the pyrrole ring), 3.77 (2H, bd, J=6 Hz, CHC$\underline{H}_2$OH), 4.06 (1H, bs, OH), 4.33 (1H, m, CH$_3$C$\underline{H}$CH$_2$), 5.93 (1H, s, H at the 4-position of the pyrrole ring), 7.20–7,50 (3H, m, H on Ph), 7.50–7.80 (2H, m, H on Ph).

$[\alpha]_D^{21} = -19.1°$ (c=0.0470, $C_2H_5OH$).

EXAMPLE 4

Synthesis of 2-(3-benzoyl-2,5-dimethylpyrrol-1-yl)ethanol (100):

In the same way as in Example 1, compound (100) was prepared in a yield of 92.9% from 2-(3-benzoyl-2,5-dimethylpyrrol-1-yl)ethyl acetate.

Melting point: 97–99° C. (recrystallized from $C_2H_5OH$),

IR (neat): 3410, 3060, 2940, 1740, 1630, 1620, 1570, 1515, 1450, 1420, 1365, 1255, 1180, 1155, 1120, 1050, 1005, 980, 930, 910, 860, 810, 790, 770, 730, 700, 665 cm$^{-1}$.

NMR (CDCl$_3$, δ(ppm)): 2.09 (3H, s, CH$_3$ at the 5-position of the pyrrole ring), 2.45 (3H, s, CH$_3$ at the 2-position of the pyrrole ring), 3.5–3.9 (4H, m, NCH$_2$CH$_2$O), 4.20 (1H, bs, OH), 5.96 (1H, s, H on the pyrrole ring), 7.2–7.5 (3H, m, H on Ph), 7.5–7.75 (2H, m, H on Ph).

Mass spectrum (70 eV; m/e, %): 244 (M+1, 12), 243 (M$^+$, 77), 242 (48), 228 (4), 227 (3), 226 (4), 224 (3), 212 (8), 200 (6), 199 (37), 198 (19), 197 (12), 166 (40), 138 (10), 122 (20), 121 (10), 106 (15), 105 (100), 94 (9), 85 (17), 83 (26), 77 (67), 67 (10), 66 (8), 65 (10), 53 (10), 51 (18), 45 (14), 42 (17).

EXAMPLE 5

Synthesis of 2-(3-p-chlorobenzoyl-2,5-dimethylpyrrol-1-yl)ethanol (120):

In the same way as in Example 1, compound (120) was prepared in a yield of 88.2% from 2-(3-p-chlorobenzoyl-2,5-dimethylpyrrol-1-yl)ethyl acetate.

IR (neat): 3400, 2930, 1735, 1620, 1590, 1560, 1515, 1485, 1420, 1360, 1250, 1170, 1090, 1050, 1010, 910, 860, 845, 760 cm$^{-1}$.

NMR (CDCl$_3$, δ(ppm)): 2.16 (3H, s, CH$_3$ at the 5-position of the pyrrole ring), 2.50 (3H, s, CH$_3$ at the 2-position of the pyrrole ring), 3.58 (1H, bs, alcoholic H), 3.65–4.05 (4H, m, —CH$_2$CH$_2$—), 6.02 (1H, s, H at the 4-position of the pyrrole ring), 7.44 and 7.71 (2H and 2H, d×2, J=8 Hz, H on Ph).

EXAMPLE 6

Synthesis of 2-(3-benzoyl-2,5-dimethylpyrrol-1-yl)-2-ethylethanol (112):

In the same way as in Example 1, compound (112) was prepared in a yield of 92.8% from 2-(3-benzoyl-2,5-dimethylpyrrol-1-yl)-2-ethylethyl acetate.

Melting point: 114–115° C.

IR (neat): 3450, 1610, 1569, 1508, 1420, 1312, 1250, 901, 735 cm$^{-1}$.

NMR (CDCl$_3$, δ(ppm)):
0.82 (3H, t, J=7 Hz, CH$_2$C$\underline{H}_3$), 1.79 (2H, m, J=7 Hz, C$\underline{H}_2$CH$_3$), 2.17 (3H, s, CH$_3$ at the 5-position of the pyrrole ring), 2.54 (3H, s, CH$_3$ at the 2-position of the pyrrole ring), 2.60 (1H, bs, OH), 3.7–4.3 (3H, m, NC$\underline{H}$C$\underline{H}_2$O), 5.98 (1H, s, H on the pyrrole ring), 7.30–7.60 (3H, m, H on Ph), 7.60–7.80 (2H, m, H on Ph).

EXAMPLE 7

Synthesis of 2-(3-benzoyl-2,5-dimethylpyrrol-1-yl)-2-isobutylethanol (116):

In the same way as in Example 1, compound (116) was prepared in a yield of 100% from 2-(3-benzoyl-2,5-dimethylpyrrol-1-yl)-2-isobutylethyl acetate.

IR (neat): 3400, 3060, 2940, 2860, 1630, 1620, 1570, 1510, 1465, 1450, 1420, 1320, 1255, 1185, 1175, 1160, 1105, 1070, 1050, 1030, 930, 910, 860, 810, 790, 775, 730, 695 cm$^{-1}$.

NMR (CDCl$_3$, δ (ppm)): 0.88 (6H, d, J=5 Hz, CH$_3$), 1.40–2.00 (3H, m, C$\underline{H}_2$C$\underline{H}$ Me$_2$), 2.19 (3H, s, CH$_3$ at the 5-position of the pyrrole ring), 2.56 (3H, s, CH$_3$ at the 2-position of the pyrrole ring), 3.40–4.60 (4H, m, NC$\underline{H}$C$\underline{H}_2$O$\underline{H}$), 5.99 (1H, s, H on the pyrrole ring), 7.25–7.50 (3H, m, H on Ph), 7.50–7.80 (2H, m, H on Ph).

EXAMPLE 8

Synthesis of 2-(3-benzoyl-2,5-dimethylpyrrol-1-yl)-2-methyl-1-phenylethanol (118):

In the same way as in Example 1, compound (118) was prepared in a yield of 100% from 2-(3-benzoyl-2,5-dimethylpyrrol-1-yl)-2-methyl-1-phenylethyl acetate.

IR (neat): 3410, 3070, 3000, 2950, 1740, 1620, 1605, 1575, 1520, 1450, 1420, 1395, 1310, 1255, 1195, 1180, 1160, 1080, 1060, 1030, 1000, 935, 915, 900, 810, 795, 760, 735, 700 cm$^{-1}$.

NRM (CDCl$_3$, δ (ppm)): 1.60 (3H, d, J=7 Hz, CH-C$\underline{H}_3$), 2.05 (6H, bs, CH$_3$on the 2- and 5-positions of the pyrrole ring), 3.75 (1H, bs, OH), 4.25 (1H, m, N—C$\underline{H}$—CH$_3$), 4.87 (1H, d, J=9 Hz, CHC$\underline{H}$OH), 5.81 (1H, s, H on the pyrrole ring), 7.10 (5H, bs, Ph) 7.17-7.57 (5H, m, Ph).

EXAMPLE 9

Synthesis of 2-(3-benzoyl-2,5-dimethylpyrrol-1-yl)-1-ethylethanol (104):

In the same way as in Example 1, compound (104) was prepared in a yield of 93.7% from 2-(3-benzoyl-2,5-dimethylpyrrol-1-yl)-1-ethylethyl acetate.

Melting point: 107°-107.5° C.

IR (Kbr): 3420, 1613, 1570, 1513, 1420, 730 cm$^{-1}$.

NMR (CDCl$_3$, δ(ppm)): 0.97 (3H, t, J=7 Hz, C$\underline{H}_2$CH$_3$), 1.45 (2H, m, CHC$\underline{H}_2$CH$_3$), 2.11 (3H, s, CH$_3$ at the 5-position of the pyrrole ring), 2.45 (3H, s, CH$_3$ at the 2-position of the pyrrole ring), 2.65 (1H, s, OH), 3.75 (3H, bs, NC$\underline{H}_2$CHO—), 6.00 (1H, s, H on the pyrrole ring), 7.3-7.6 (3H, m, H on Ph), 7.6-7.8 (2H, m, H on Ph).

EXAMPLE 10

In the same way as in Example 1, compounds (102), (114), (122), (124), (126), (128) and (130) were prepared.

EXAMPLE 11

Synthesis of 2-(3-benzoyl-2,5-dimethylpyrrol-1-yl)-2-methylethyl methyl ether (206):

Sodium hydride (50% content, 115 mg, 2.3 mmoles) was washed with 20 ml of petroleum ether twice, and 15 ml of dimethoxyethane was added. To the mixture was added 300 mg (1.17 mmoles) of 2-(3-benzoyl-2,5-dimethylpyrrol-1-yl)-2-methylethanol, and the mixture was stirred at room temperature for 2 hours. Then, 5 ml of methyl iodide was added, and the mixture was further stirred at room temperature for 5 hours. After the reaction, the reaction mixture was extracted with ethyl acetate. The organic layer was washed with water, dried over anhydrous magnesium sulfate, and concentrated to afford 270 mg of a crude product. The product was chromatographed on a column of silica gel using cyclohexane/ethyl acetate (4/1) as an eluent to afford compound (206) (220 mg, 0.81 mmole, 69.4%).

IR (neat): 3050, 2980, 2940, 2900, 2840, 1740, 1635, 1600, 1575, 1520, 1450, 1420, 1375, 1320, 1300, 1250, 1190, 1180, 1110, 1075, 1050, 1030, 1010, 960, 930, 910, 810, 790, 775, 730, 695 cm$^{-1}$.

NMR (CDCl$_3$, δ (ppm)): 1.43 (3H, d, J=7 Hz, CH—C$\underline{H}_3$), 2.18 (3H, s, CH$_3$ at the 5-position of the pyrrole ring), 2.57 (3H, s, CH$_3$ at the 2-position of the pyrrole ring), 3.23 (3H, s, OCH$_3$), 3.58 (2H, d, J=7 Hz, CHC$\underline{H}_2$O), 4.46 (1H, sextet, J=7 Hz, NC$\underline{H}$CH$_2$), 5.97 (1H, s, H on the pyrrole ring), 7.20-7.45 (3H, m, H on Ph), 7.60-7.80 (2H, m, H on Ph).

Mass spectrum (70 eV; m/e, %): 272 (M+1, 10), 271 (M$^+$, 50), 270 (9), 256 (2), 240 (3), 226 (9), 200 (11), 199 (75), 198 (20), 194 (8), 148 (3), 122 (12), 121 (6), 120 (5), 106 (9), 105 (100), 77 (32), 73 (14), 72 (14), 45 (18), 41 (16).

EXAMPLE 12

Synthesis of (2R)-2-(3-benzoyl-2,5-dimethylpyrrol-1-yl)-2-methylethyl methyl ether (210):

In the same way as in Example 11, compound (210) was prepared in a yield of 71.3% from (2R)-2-(3-benzoyl-2,5-dimethylpyrrol-1-yl)-2-methylethanol. [α]$_D^{22}$ =+0.69° (c=0.0494, C$_2$H$_5$OH). The IR (neat), and NMR (CDCl$_3$) data of the product were identical with those of compound (206) prepared in Example 11.

EXAMPLE 13

Synthesis of 2-(3-benzoyl-2,5-dimethylpyrrol-1-yl)-2-ethylethyl methyl ether (212):

In the same way as in Example 11, compound (212) was prepared in a yield of 91% from 2-(3-benzoyl-2,5-dimethylpyrrol-1-yl)-2-ethylethanol.

Melting point: 88°-89° C. (recrystallized from cyclohexane).

IR (CHCl$_3$ solution): 1629, 1570, 1510, 1445, 1412 cm$^{-1}$.

NMR (CDCl$_3$, δ(ppm)): 0.82 (3H, t, J=7 Hz, CH$_2$C$\underline{H}_3$), 1.86 (2H, dq, J=7 Hz, C$\underline{H}_2$CH$_3$), 2.18 (3H, s, CH$_3$ at the 5-position of the pyrrole ring), 2.58 (3H, s, CH$_3$ at the 2-position of the pyrrole ring), 3.27 (3H, s, OCH$_3$), 3.64 (2H, d, J=7 Hz, —CH$_2$O—), 4.25 (1H, tt, J=7 Hz, NC$\underline{H}$CH$_2$O), 6.01 (1H, s, H on the pyrrole ring), 7.15-7.9 (5H, m. Ph).

EXAMPLE 14

Synthesis of 2-(3-benzoyl-2,5-dimethylpyrrol-1-yl)-2-methyl-1-phenylethyl methyl ether (218):

In the same way as in Example 11, compound (218) was prepared in a yield of 72.9% from 2-(3-benzoyl-2,5-dimethylpyrrol-1-yl)-2-methyl-1-phenylethanol.

IR (neat): 3060, 2990, 2940, 2820, 1740, 1635, 1605, 1575, 1515, 1450, 1420, 1395, 1350, 1310, 1250, 1200, 1180, 1160, 1100, 1075, 1040, 1030, 1000, 970, 930, 910, 810, 790, 760, 730, 700, 670 cm$^{-1}$.

NMR (CDCl$_3$, δ(ppm)): 1.63 (3H, d, J=6 Hz, CH—C$\underline{H}_3$), 2.07 (3H, s, CH$_3$ at the 5-position of the pyrrole ring), 2.37 (3H, s, CH$_3$ at the 2-position of the pyrrole ring), 3.24 (3H, s, OCH$_3$), 4.0-4.57 (2H, m, NC$\underline{H}$ C$\underline{H}$O), 5.90 (1H, bs, H on the pyrrole ring), 7.17 (5H, bs, Ph), 7.27-7.47 (3H, m. H on Ph), 7.47-7.73 (2H, m, H on Ph).

Mass spectrum (70 eV; m/e, %): 348 (M+1, 7), 347 (M$^+$, 29), 272 (2), 227 (9), 226 (48), 199 (10), 148 (8), 122 (8), 121 (71), 117 (8), 115 (6), 106 (8), 105 (100), 91 (12), 77 (34).

EXAMPLE 15

Synthesis of 2-(3-benzoyl-2,5-dimethylpyrrol-1-yl)-1-ethylethyl methyl ether (204):

In the same way as in Example 11, compound (204) was prepared in a yield of 60% from 2-(3-benzoyl-2,5-dimethylpyrrol-1-yl)-1-ethylethanol.

Melting point: 65°-66° C. (recrystallized from cyclohexane).

IR (CHCl$_3$ solution): 1629, 1572, 1511, 1544, 1414, 1363 cm$^{-1}$.

NMR (CDCl$_3$, δ (ppm)): 0.96 (3H, 5 J=6.5 Hz, CH$_2$CH$_3$), 1.25-1.7 (2H, m, CH$_2$CH$_3$), 2.18 (3H, s, CH$_3$ at the 5-position of the pyrrole ring), 2.56 (3H, s, CH$_3$ at the 2-position of the pyrrole ring), 3.11 (3H, s, OCH$_3$), 3.1-3.47 (1H, m, CH$_2$CHO), 3.7-3.9 (2H, m, NCH$_2$CH), 6.03 (1H, s, H on the pyrrol ring), 7.2-7.9 (5H, m, Ph).

EXAMPLE 16

Synthesis of 2-(3-benzoyl-2,5-dimethylpyrrol-1-yl)ethyl methyl ether (200):

Benzoic anhydride (6.78 g, 30.0 mmoles) and 0.5 ml of 52% aqueous hydriodic acid were added to 3.06 g (20.0 mmoles) of 2-(2,5-dimethylpyrrol-1-yl)ethyl methyl ether obtained by the dehydration cyclization of acetonylacetone and 2-methoxyethylamine. The mixture was heated in an atmosphere of nitrogen at 130° C. for 5 hours, and heated at 150° C. for 2 hours. To the reaction mixture were added 100 ml of 5% aqueous sodium hydroxide and 50 ml of ethanol, and the mixture was stirred at room temperature for 3 hours to decompose the unreacted benzoic anhydride. The ethanol was distilled off under reduced pressure. The residue was extracted with ethyl acetate, and the resulting extract was washed with an aqueous solution of sodium hydrogen carbonate, dried over anhydrous magnesium sulfate, and concentrated to afford 3.34 g of a crude product. The product was chromatographed on a column of silica gel using cyclohexane/ethyl acetate (3/1) as an eluent to afford compound (200) (1.16 g, 4.51 mmoles, 22.6%) with the recovery of 580 mg (3.79 mmoles, 19.0%) of the starting material.

Melting point: 99°-100° C. (recrystallized from cyclohexane).

IR (KBr): 3090, 2990, 2920, 2840, 1625, 1600, 1570, 1515, 1450, 1420, 1365, 1260, 1200, 1190, 1155, 1125, 1100, 1080, 1045, 1030, 1005, 985, 940, 910, 855, 835, 810, 780, 770, 735, 700, 660 cm$^{-1}$.

NMR (CDCl$_3$, δ(ppm)): 2.17 (3H, s, CH$_3$ at the 5-position of the pyrrole ring), 2.53 (3H, s, CH$_3$ at the 2-position of the pyrrole ring), 3.31 (3H, s, OCH$_3$), 3.51 (2H, t, J=6 Hz, —CH$_2$O—), 3.97 (2H, t, J=6 Hz, —NCH$_2$—), 6.01 (1H, s, H on the pyrrole ring), 7.30-7.50 (3H, m. H on Ph), 7.63-7.83 (2H, m, H on Ph).

Mass spectrum (70 eV; m/e, %): 258 (M+1, 13), 257 (M+, 75), 256 (31), 242 (9), 226 (8), 224 (4), 212 (7), 200 (6), 199 (37), 198 (15), 180 (12), 152 (6), 122 (16), 106 (13), 105 (100), 77 (42), 59 (12), 51 (9).

EXAMPLE 17

Synthesis of 2-(3-isobutyryl-2,5-dimethylpyrrol-1-yl)-ethyl methyl ether (230):

Compound (230) was prepared in a yield of 56.1% by reacting 2-(2,5-dimethylpyrrol-1-yl)ethyl methyl ether with isobutyric anhydride under the similar reaction conditions as in Example 16.

IR (neat): 3100, 2980, 2940, 2890, 1740, 1650, 1580, 1520, 1450, 1420, 1395, 1420, 1370, 1325, 1285, 1240, 1210, 1195, 1150, 1125, 1095, 1030, 1005, 955, 870, 830, 790, 760, 705 cm$^{-1}$.

NMR (CDCl$_3$, δ(ppm)): 1.10 (6H, d, J=7 Hz, CHCH$_3$), 2.17 (3H, s, CH$_3$ at the 5-position of the pyrrole ring), 2.51 (3H, s, CH$_3$ at the 2-position of the pyrrole ring), 3.13 (1H, m, COCH CH$_3$), 3.26 (3H, s, OCH$_3$), 3.47 (2H, t, J=5 Hz, —CH$_2$O), 3.91 (2H, t, J=5 Hz, NCH$_2$—), 6.17 (1H, s, H on the pyrrole ring).

EXAMPLE 18

Synthesis of 2-(3-pivaloyl-2,5-dimethylpyrrol-1-yl)ethyl methyl ether (232):

Compound (232) was prepared in a yield of 71.3% by reacting 2-(2,5-dimethylpyrrol-1-yl)ethyl methyl ether with pivalic anhydride under the same reaction conditions as in Example 16.

IR (neat): 2950, 1740, 1640, 1575, 1510, 1480, 1455, 1420, 1365, 1265, 1240, 1200, 1170, 1145, 1120, 1100, 1030, 1005, 970, 940, 930, 835, 810, 790, 770, 760 cm$^{-1}$.

NMR (CDCl$_3$, δ(ppm)): 1.29 (9H, s, tBu), 2.20 (3H, s, CH$_3$ at the 5-position of the pyrrole ring), 2.47 (3H, s, CH$_3$ at the 2-position of the pyrrole ring), 3.27 (3H, s, OCH$_3$), 3.49 (2H, t, J=5 Hz, —CH$_2$O), 3.93 (2H, t, J=5 Hz, —NCH$_2$—), 6.30 (1H, s, H on the pyrrole ring).

EXAMPLE 19

Synthesis of 2-(3-cyclohexylcarbonyl-2,5-dimethylpyrrol-1-yl)ethyl methyl ether (234):

Compound (234) was prepared in a yield of 55.5% by reacting 2-(2,5-dimethylpyrrol-1-yl)ethyl methyl ether with cyclohexanecarboxylic anhydride under the same conditions as in Example 16.

IR (neat): 2940, 2850, 1740, 1645, 1575, 1520, 1450, 1420, 1395, 1370, 1305, 1290, 1240, 1200, 1170, 1120, 1100, 1030, 1000, 960, 920, 890, 860, 830, 810, 780, 750, 720 cm$^{-1}$.

NMR (CDCl$_3$, δ(ppm)): 1.0-1.9 (10H, m, H on cyclohexane) 2.17 (3H, s, CH$_3$ at the 5-position of the pyrrole ring), 2.50 (3H, s, CH$_3$ at the 2-position of the pyrrole ring), 3.0 (1H, m, —CHCO—), 3.24 (3H, s, OCH$_3$), 3.46 (2H, t, J=5 Hz, —CH$_2$O—), 3.89 (2H, t, J=5 Hz, —NCH$_2$—), 6.17 (1H, s, H on the pyrrole ring).

EXAMPLE 20

Synthesis of 2-(3-o-methylbenzoyl-2,5-dimethylpyrrol-1-yl)ethyl methyl ether (238):

Compound (238) was prepared in a yield of 47.6% by reacting 2-(2,5-dimethylpyrrol-1-yl)ethyl methyl ether with o-toluic anhydride under the same reaction conditions as in Example 16.

IR (neat): 3050, 2980, 2930, 2900, 1740, 1630, 1605, 1575, 1515, 1450, 1420, 1360, 1285, 1250, 1195, 1150, 1120, 1090, 1040, 1030, 1000, 980, 910, 830, 780, 760, 745, 700 cm$^{-1}$.

NMR (CDCl$_3$, δ(ppm)): 2.07 (3H, s, CH$_3$ at the 5-position of the pyrrole ring), 2.25 (3H, s, CH$_3$ of the tolyl group), 2.45 (3H, s, CH$_3$ at the 2-position of the pyrrole ring), 3.22 (3H, s, OCH$_3$), 3.47 (2H, t, J=5 Hz, —CH$_2$O—), 3.90 (2H, t, J=5 Hz, —NCH$_2$—), 5.78 (1H, s, H on the pyrrole ring), 7.18 (4H, bs, H of the tolyl group).

EXAMPLE 21

Synthesis of 2-(3-m-chlorobenzoyl-2,5-dimethylpyrrol-1-yl)ethyl methyl ether (242):

Compound (242) was prepared in a yield of 27.4% by reacting 2-(2,5-dimethylpyrrol-1-yl)ethyl methyl ether with m-chlorobenzoic anhydride under the same conditions as in Example 16.

Melting point: 112°-113° C. (recrystallized from cyclohexane).

IR (KBr): 3050, 1740, 1615, 1560, 1510, 1465, 1410, 1355, 1275, 1240, 1185, 1155, 1120, 1075, 1045, 1030, 1000, 980, 930, 920, 895, 830, 810, 800, 755, 730, 700, 680 cm$^{-1}$.

NMR (CDCl$_3$, δ(ppm)): 2.17 (3H, s, CH$_3$ at the 5-position of the pyrrole ring), 2.53 (3H, s, CH$_3$ at the 2-position of the pyrrole ring), 3.27 (3H, s, OCH$_3$), 3.51 (2H, t, J=5 Hz, —CH$_2$O—), 3.96 (2H, t, J=5 Hz, —NCH$_2$—), 5.97 (1H, s, H on the pyrrole ring), 7.20–7.75 (4H, m, H on Ph).

EXAMPLE 22

Synthesis of 2-(3-p-methoxybenzoyl-2,5-dimethylpyrrol-1-yl)ethyl methyl ether (244):

Compound (244) was prepared in a yield of 28.9% by reacting 2-(2,5-dimethylpyrrol-1-yl)ethyl methyl ether with p-anisic anhydride under the same conditions as in Example 16.

IR (neat): 2940, 2900, 2840, 1740, 1630, 1605, 1580, 1520, 1510, 1425, 1395, 1370, 1305, 1255, 1170, 1125, 1030, 1005, 910, 850, 800, 770, 710 cm$^{-1}$.

NMR (CDCl$_3$, δ(ppm)): 2.17 (3H, s, CH$_3$ at the 5-position of the pyrrole ring), 2.50 (3H, s, CH$_3$ at the 2-position of the pyrrole ring), 3.27 (3H, s, CH$_2$OCH$_3$), 3.50 (2H, t, J=5 Hz, —CH$_2$O—), 3.78 (3H, s, PhOCH$_3$), 3.94 (2H, t, J=5 Hz, —NCH$_2$—), 6.03 (1H, s, H on the pyrrole ring), 6.87 (2H, d, J=9 Hz, ortho protons of MeO on Ph), 7.77 (2H, d, J=9 Hz, meta protons of MeO on Ph).

EXAMPLE 23

Synthesis of 2-[3-(2-furoyl)-2,5-dimethylpyrrol-1-yl]-ethyl methyl ether (250):

Compound (250) was prepared in a yield of 4.1% by reacting 2-(2,5-dimethylpyrrol-1-yl)ethyl methyl ehter with 2-furoic anhydride under the same conditions as in Example 16.

IR (neat): 3430, 3120, 2940, 1710, 1620, 1580, 1565, 1515, 1470, 1420, 1360, 1300, 1270, 1225, 1200, 1170, 1120, 1060, 1020, 980, 940, 885, 870, 830, 765 cm$^{-1}$.

NMR (CDCl$_3$, δ(ppm)): 2.19 (3H, s, CH$_3$ at the 5-position of the pyrrole ring), 2.55 (3H, s, CH$_3$ at the 2-position of the pyrrole ring), 3.29 (3H, s, OCH$_3$), 3.51 (2H, t, J=6 Hz, —CH$_2$O—), 3.87 (2H, t, J=6 Hz, —NCH$_2$—), 5.73 (1H, s, H on the pyrrole ring), 6.51 (1H, m, H on the furan ring), 7.14 (1H, m, H on the furan ring), 7.54 (1H, m, H on the furan ring).

EXAMPLE 24

Synthesis of 2-[3-(2-thenoyl)-2,5-dimethylpyrrol-1-yl]-ethyl methyl ether (252):

Compound (252) was prepared in a yield of 30.4% by reacting 2-(2,5-dimethylpyrrol-1-yl)ethyl methyl ether with 2-thenoic anhydride under the same reaction conditions as in Example 16.

IR (neat): 3090, 2980, 2920, 2880, 2830, 1735, 1610, 1570, 1520, 1420, 1365, 1275, 1250, 1195, 1150, 1120, 1090, 1045, 1000, 980, 895, 875, 845, 795, 760, 720, 670 cm$^{-1}$.

NMR (CDCl$_3$, δ(ppm)): 2.20 (3H, s, CH$_3$ at the 5-position of the pyrrole ring), 2.51 (3H, s, CH$_3$ at the 2-position of the pyrrole ring), 3.27 (3H, s, OCH$_3$), 3.50 (2H, t, J=5 Hz, —CH$_2$O—), 3.95 (2H, t, J=5 Hz, —NCH$_2$—), 6.31 (1H, s, H on the pyrrole ring), 7.04 (1H, dd, J=3 & 4 Hz, H on the thiophene ring), 7.50 (1H, dd, J=4 & 1 Hz, H on the thiophene ring), 7.68 (1H, dd, J=3 & 1 Hz, H on the thiophene ring).

Mass Spectrum (70 eV; m/e, %): 254 (M+1, 12), 263 (M+, 68), 262 (13), 248 (6), 232 (4), 230 (6), 218 (12), 205 (30) 204 (10), 180 (6), 122 (12), 111 (100), 106 (6), 65 (6), 59 (8), 39 (11).

EXAMPLE 25

Synthesis of 2-(3-nicotinoyl-2,5-dimethylpyrrol-1-yl)ethyl methyl ether (260):

In 1,2-dichloroethane, 2-(2,5-dimethylpyrrol-1-yl)-ethyl methyl ether was reacted with nicotinoyl chloride hydrochloride in the presence of aluminum chloride. The reaction product was chromatographed on a column of silica gel using cyclohexane/ethyl acetate (1/1) as an eluent to afford compound (260) in a yield of 13.2%.

IR (neat): 3050, 3000, 2940, 2900, 1740, 1635, 1590, 1520, 1420, 1365, 1260, 1200, 1160, 1120, 1100, 1045, 1030, 1005, 985, 970, 910, 830, 795, 750, 715 cm$^{-1}$.

NMR (CDCl$_3$, δ(ppm)): 2.17 (3H, s, CH$_3$ at the 5-position of the pyrrole ring), 2.56 (3H, s, CH$_3$ at the 2-position of the pyrrole ring), 3.27 (3H, s, OCH$_3$), 3.53 (2H, t, J=6 Hz, —CH$_2$O—), 3.98 (2H, t, J=6 Hz, —NCH$_2$—), 6.00 (1H, s, H on the pyrrole ring), 7.33 (1H, dd, J=5 & 8 Hz, H on the pyridine ring), 8.03 (1H, dt, J=2 & 8 Hz, H on the pyridine ring), 8.65 (1H, dd, J=2 & 5 Hz, H on the pyridine ring), 8.95 (1H, d, J=2 Hz, H on the pyridine ring).

EXAMPLE 26

Synthesis of 2-(3-benzoyl-2,5-dimethylpyrrol-1yl)ethyl phenyl ether (226):

Compound (226) was prepared in a yield of 38% by reacting 2-(2,5-dimethylpyrrol-1-yl)ethyl phenyl ether (obtained by the dehydration cyclization of acetonylacetone and 2-phenoxyethylamine) with benzoic anhydride under the same conditions as in Example 16.

Melting point: 130°–131.5° C. (recrystallized from benzene.

IR (CHCl$_3$ solution): 1629, 1603, 1574, 1510, 1495, 1444, 1414, 1361 cm$^{-1}$.

NMR (CDCl$_3$, δ(ppm)): 2.24 (3H, s, CH$_3$ at the 5-position of the pyrrole ring), 2.60 (3H, s, CH$_3$ at the 2-position of the pyrrole ring), 4.0–4.3 (4H, m , NCH$_2$CH$_2$O), 6.06 (1H, s, H on the pyrrole ring), 6.70–7.90 (10H, m, H on Ph).

EXAMPLE 27

Compounds (202), (208), (214), (216), (220), (222), (224), (228), (236), (240), (246), (248), (254), (256), (258), and (262) to (294) were synthesized in the same way as in Example 11 or 16.

EXAMPLE 28

Synthesis of 2-(3-benzoyl-2,5-dimethylpyrrol-1-yl)-2-methylethyl acetate (306):

Benzoic anhydride (5.44 g, 24.0 mmoles) was added to 2-(2,5-dimethylpyrrol-1-yl)propyl acetate (1.95 g, 10.0 mmoles) obtained in Referential Example 2, and 0.1 ml of 52% aqueous hydriodic acid was added. The mixture was heated 100° C. for 6 hours in an atmosphere of nitrogen. Then, 50 ml of 1.0 N sodium hydroxide was added to the reaction mixture, and the mixture extracted with 50 ml of ethyl acetate three times. The organic layer was dried over anhydrous magnesium sulfate, and concentrated to afford 4.86 g of a crude product. The product was chromatographed on a column of silica gel using cyclohexane/ethyl acetate (3/1) as an eluent to afford compound (306) (1.26 g, 4.21 mmoles, 42.1%) with the recovery of 490 mg (2.51 mmoles, 25.1%) of the starting material.

IR (neat): 2980, 1745, 1635, 1605, 1520, 1425, 1250, 1175, 910, 730, 700 cm$^{-1}$.

NMR (CDCl$_3$, δ(ppm)): 1.47 (3H, d, J=7 Hz, CHCH$_3$), 1.91 (3H, s, OCOCH$_3$), 2.20 (3H, s, CH$_3$ at the 5-position of the pyrrole ring), 2.57 (3H, CH$_3$ at the 2-position of the pyrrole ring), 4.10–4.80 (3H, m, NCHCH$_2$O), 5.95 (1H, s, H on the pyrrole ring), 7.25–7.50 (3H, m, H on Ph), 7.60–7.85 (2H, m, H on Ph).

Mass spectrum (70 eV; m/e, %): 300 (M+1, 11), 299 (M+, 57), 298 (20), 284 (2), 256 (4), 240 (6), 238 (4), 226 (4), 222 (5), 200 (6), 199 (36), 198 (27), 197 (11), 122 (13), 105 (100), 101 (23), 77 (37), 43 (68).

EXAMPLE 29

Synthesis of (2S)-2-(3-benzoyl-2,5-dimethylpyrrol-1yl)-2-methylethyl acetate (316):

Compound (316) was prepared in a yield of 42.8% using (2S)-2-(2,5-dimethylpyrrol-1-yl)-2 methylethyl acetate ([α]$_D^{21}$=−5.17°, c=0.027, C$_2$H$_5$OH) as a starting material in the same way as in Example 28. The IR, NMR and mass spectra of this product were identical with those of the product (306) of Example 28.

[α]$_D^{21}$=+11.7° (c=0.0174, C$_2$H$_5$OH).

EXAMPLE 30

Synthesis of (2R)-2-(3 benzoyl-2,5-dimethylpyrrole-1yl)-2-methylethyl acetate (318):

In the same way as in Example 28, compound (318) was prepared in a yield of 67.2% from (2R)-2-(2,5-dimethylpyrrol-1-yl)-2-methylethyl acetate ([α]$_D^{21}$=+6.04°, c=0.0570, C$_2$H$_5$OH) as a starting material. The IR, NMR and mass spectra of this product were identical with those of the product (306) in Example 28.

[α]$_D^{21}$=−13.7° (c=0.0182, C$_2$H$_5$OH).

EXAMPLE 31

Synthesis of 2-(3-benzoyl-2,5-dimethylpyrrol-1-yl)ethyl acetate (300):

In the same way as in Example 28, compound (300) was prepared in a yield of 29.4% from 2-(2,5-dimethylpyrrol-1-yl)ethyl acetate as a starting material.

Melting point: 91°–93° C. (recrystallized from ethanol).

IR (neat): 3050, 2950, 1745, 1630, 1600, 1575, 1520, 1450, 1420, 1390, 1370, 1245, 1190, 1175, 1160, 1100, 1060, 1010, 980, 935, 910, 850, 810, 790, 730, 700, 665 cm$^{-1}$ NMR (CDCl$_3$, δ(ppm)): 1.97 (3H, s, OCOCH$_3$), 2.16 (3H, s, CH$_3$ at the 5-position of the pyrrole ring), 2.51 (3H, s, CH$_3$ at the 2-position of the pyrrole ring), 3.85–4.25 (4H, m. NCH$_2$CH$_2$O), 6.02 (1H, s, H on the pyrrole ring), 7.2–7.5 (3H, m, H on Ph), 7.6–7.8 (2H, m, H on Ph).

EXAMPLE 32

Synthesis of 2-(3-benzoyl-2,5-dimethylpyrrol-1-yl)-2-methyl-1 phenylethyl acetate (328):

In the same way as in Example 28, compound (328) was prepared in a yield of 33.1% from 2-(2,5-dimethylpyrrol-1-yl)-2-methyl-1-phenylethyl acetate as a starting material.

IR (neat): 3050, 2990, 2940, 1745, 1635, 1600, 1575, 1515, 1450, 1415, 1370, 1310, 1245, 1230,, 1180, 1160, 1100, 1075, 1045, 1030, 1000,, 930, 910, 760, 730, 700 cm−1.

NMR (CDCl$_3$, δ(ppm): 1.57 (1H, d, J=10 Hz, CHCH$_3$), 2.06 (6H, s, CH$_3$ at 2- and 5-positions of the pyrrole ring), 2.33 (3H, s, OCOCH$_3$), 4.5 (1H, m, NCH—), 5.93 (1H, s, H on the pyrrole ring), 6.10 (1H, d, J=10 Hz, PhCHO), 7.13 (5H, bs, Ph), 7.20–7.50 (3H, m, H on Ph), 7.50–7.75 (2H, m, H on Ph),

EXAMPLE 33

Synthesis of 2-(3-benzoyl-2,5-dimethylpyrrol-1-yl)-2-isobutylethyl acetate (326):

In the same way as in Example 28, compound (326) was prepared in a yield of 41.1% from 2-(2,5-dimethylpyrrol-1-yl)-2-isobutylethyl acetate as a starting material.

IR (neat): 3060, 2970, 2880, 1750, 1635, 1600, 1580, 1520, 1450, 1420, 1405, 1370, 1320, 1245, 1195, 1180, 1080, 1045, 935, 910, 810, 790, 780, 730, 700 cm$^{-1}$ NMR (CDCl$_3$, δ(ppm): 0.89 (6H, d, J=5 Hz, CHCH$_3$), 1.2–1.9 (3H, m, CHCH$_2$CHMe$_2$), 1.91 (3H, s, OCOCH$_3$), 2.20 (3H, s, CH$_3$ at the 5-position of the pyrrole ring), 2.56 (3H, s, CH$_3$ at the 2-position of the pyrrole ring), 4.10–4.60 (3H, m, NCHCH$_2$O), 5.98 (1H, s, H on the pyrrole ring), 7.20–7.50 (3H, m, H on Ph), 7.55–7.83 (2H, m, H on Ph).

EXAMPLE 34

Synthesis of 2-(3-benzoyl-2,5-dimethylpyrrol-1-yl)-2-methylethyl benzoate (314):

In 10 ml of methylene chloride were dissolved 140 mg (0.54 mmole) of 2-(3-benzoyl-2,5-dimethylpyrrol-1-yl) 2-methylethanol and 383 mg (2.75 mmoles) of benzoyl chloride. Triethylamine (1 ml) was added to the solution, and the mixture was stirred at room temperature for 20 hours. Chloroform was added to the reaction mixture. The mixture was washed with dilute hydrochloric acid and then with an aqueous solution of sodium hydrogen carbonate, and the resulting extract was dried over anhydrous magnesium sulfate, and concentrated to afford 860 mg of a crude product. The product was chromatographed on a column of silica gel using cyclohexane/ethyl acetate (3/1) as an eluent to afford compound (314) (150 mg, 0.42 mmole, 77.8%).

IR (neat): 3060, 2990, 2950, 1730, 1635, 1605, 1580, 1520, 1455, 1420, 1380, 1320, 1305, 1280, 1250, 1200, 1180, 1110, 1075, 1030, 985, 935, 910, 810, 795, 780, 730, 715, 700 cm$^{-1}$.

NMR (CDCl$_3$, δ(ppm)): 1.52 (3H, d, J=6 Hz, $$\underset{CH_3CH-}{|}),$$

2.21 (3H, s, CH₃ at the 5-position of the pyrrole ring), 2.57 (3H, s, CH₃ at the 2-position of the pyrrole ring), 4.53 (3H, m,

5.92 (1H, s, H at the 4-position of the pyrrole ring), 7.37 and 7.60–8.00 (6H and 4H, m, H on Ph).

EXAMPLE 35

Synthesis of 2-(3-benzoyl-2,5-dimethylpyrrol-1-yl)-2-methylethyl valerate (310):

Compound (310) was prepared in a yield of 70.2% by performing the same reaction as in Example 34 except that valeryl chloride was used instead of benzoyl chloride.

IR (neat): 3060, 2980, 2880, 1745, 1640, 1610, 1580, 1520, 1450, 1424, 1410, 1380, 1320, 1250, 1200, 1180, 1115, 1100, 1050, 1030, 935, 910, 810, 795, 780, 730, 700 cm⁻¹.

NMR (CDCl₃, δ(ppm): 0.83 (3H, t, J=6 Hz, (CH₂)₃CH₃), 1.48 (3H, d, J=6 Hz, CHCH₃), 1.2–1.6 (4H, m, CH₂CH₂CH₂CH₃), 2.1–2.3 (2H, OCOCH₂—), 2.22 (3H, s, CH₃ at the 5-position of the pyrrole ring), 2.59 (3H, s, CH₃ at the 2-position of the pyrrole ring), 4.10–4.80 (3H, m, NCHCH₂O), 6.01 (1H, s, H on the pyrrole ring), 7.2–7.5 (3H, m, H on Ph), 7.6–7.85 (2H, m, H on Ph).

EXAMPLE 36

Synthesis of 2-(3-benzoyl-2,5-dimethylpyrrol-1-yl)-2-methylethyl decanoate (312):

Compound (312) was prepared in a yield of 60.3% by performing the same reaction as in Example 34 except that decanoyl chloride was used instead of benzoyl chloride.

IR (neat): 3060, 2940, 2860, 1745, 1640, 1605, 1580, 1520, 1460, 1450, 1420, 1410, 1380, 1355, 1320, 1305, 1250, 1200, 1175, 1160, 1110, 1075, 1050, 1030, 1010, 930, 910, 810, 790, 775, 730, 700 cm⁻¹.

NMR (CDCl₃, δ(ppm): 0.85 (3H, m, (CH₂)₈CH₃), 1.20 (14H, bs, OCOCH₂(CH₂)₇CH₃), 1.50 (3H, d, J=6 Hz, CH—CH₃), 2.05–2.35 (2H, OCOCH₂CH₂), 2.23 (3H, s, CH₃ at the 5-position of the pyrrole ring), 2.60 (3H, s, CH₃ at the 2-position of the pyrrole ring), 4.0–4.9 (3H, m, NCHCH₂O), 6.04 (1H, s, H on the pyrrole ring), 7.30–7.55 (3H, m, H on Ph), 7.70–7.90 (2H, m, H on Ph).

EXAMPLE 37

Synthesis of 2-(3-benzoyl-2,5-dimethylpyrrol-1-yl)-2-ethylethyl benzoate (322):

Compound (322) was prepared in a yield of 88.9% in the same way as in Example 34 using 2-(3-benzoyl-2,5-dimethylpyrrol-1-yl)-2-ethylethanol as a starting material.

IR (neat): 3060, 2990, 2900, 1730, 1635, 1605, 1575, 1520, 1450, 1420, 1400, 1375, 1320, 1275, 1250, 1180, 1115, 1105, 1070, 1050, 1030, 930, 910, 850, 810, 795, 775, 730, 710, 695 cm⁻¹.

NMR (CDCl₃, δ(ppm): 0.88 (3H, t, J=7 Hz, CH₂CH₃), 1.90 (2H, m, CH₂CH₃), 2.23 (3H, s, CH₃ at the 5-position of the pyrrole ring), 2.62 (3H, s, CH₃ at the 2-position of the pyrrole ring), 4.57 (3H, bs, NCHCH₂O), 6.03 (1H, s, H on the pyrrole ring), 7.20–7.55 (6H, m, H on Ph), 7.60–8.00 (4H, m, H on Ph).

EXAMPLE 38

Synthesis of 2-(3-p-chlorobenzoyl-2,5-dimethylpyrrol-1-yl)ethyl acetate (340):

In 1,2-dichloroethane, 2-(2,5-dimethylpyrrol-1-yl)ethyl acetate was reacted with p-chlorobenzoyl chloride in the presence of aluminum chloride at room temperature for 18 hours to afford compound (340) in a yield of 34.0%.

IR (KBr): 3400, 2960, 2850, 1735, 1675, 1620, 1590, 1510, 1415, 1365, 1350, 1320, 1245, 1230, 1170, 1130, 1090, 1050, 1010, 935, 900, 850, 840, 760 cm⁻¹.

NMR (CDCl₃, δ(ppm): 2.06 (3H, s, —OCOCH₃), 2.23 (3H, s, CH₃ at the 5-position of the pyrrole ring), 2.57 (3H, s, CH₃ at the 2-position of the pyrrole ring), 4.0–4.4 (4H, m, —CH₂CH₂—), 6.08 (1H, s, H at the 4-position of the pyrrole ring), 7.47 and 7.78 (2H and 2H, d=2, J=9 Hz, H on Ph).

EXAMPLE 39

In the same way as in Example 28, 34 or 38, compounds (302), (304), (308), (320), (324), and (330) to (338) were prepared.

EXAMPLE 40

Synthesis of 2-(3-benzoyl-2,5-dimethylpyrrol-1-yl)ethyl methyl sulfide (400):

To 1.95 g (11.54 mmoles) of 2-(2,5-dimethylpyrrol-1-yl)ethyl methyl sulfide (obtained by the dehydration cyclization of 2-methylthioethylamine and acetonylacetone) and 4.70 g (20.8 mmoles) of benzoic anhydride was added 0.1 ml of 52% aqueous hydriodic acid. The mixture was heated at 130° C. for 5.5 hours in an atmosphere of nitrogen. The reaction mixture was treated with aqueous sodium hydroxide, extracted with ethyl acetate, and the resulting extract was dried over anhydrous magnesium sulfate, and concentrated. The product was chromatographed on a column of silica gel using benzene/ethyl acetate as an eluent to afford compound (400)(780 mg, 2.88 mmoles, 25%).

Melting point: 69°–70° C. (recrystallized from cyclohexane).

IR (CHCl₃ solution): 1629, 1572, 1510, 1444, 1413, 1365 cm⁻¹.

NMR (CDCl₃, δ(ppm): 2.05 (3H, s, SCH₃), 2.18 (3H, s, CH₃ at the 5-position of the pyrrole ring), 2.55 (3H, s, CH₃ at the 2-position of the pyrrole ring), 2.5–2.85 (2H, m, —CH₂S—), 3.8–4.15 (2H, m, —NCH₂—), 6.03 (1H, s, H on the pyrrole ring), 7.2–7.85 (5H, m, Ph).

EXAMPLE 41

Synthesis of 2-(3-benzoyl-2,5-dimethylpyrrol-1-yl)ethyl phenyl sulfide (404):

Compound (404) was prepared in a yield of 43% by benzoylating 2-(2,5-dimethylpyrrol-1-yl)ethyl phenyl sulfide under the same conditions as in Example 40.

IR (CHCl₃ solution): 1628, 1573, 1508, 1413, 903 cm⁻¹.

NMR (CDCl₃, δ(ppm)): 2.01 (3H, s, CH₃ at the 5-position of the pyrrole ring), 2.38 (3H, s, CH₃ at the 2-position of the pyrrole ring), 2.75–3.15 (2H, m, —CH₂S—), 3.65–4.1 (2H, m, —NCH₂—), 5.98 (1H, s, H on the pyrrole ring), 7.0–7.5 (8H, m, H on Ph), 7.55–7.8 (2H, m, H of Ph).

EXAMPLE 42

In the same way as in Example 40, compounds (402) and (406) were synthesized.

EXAMPLE 43

Synthesis of 2-(3-benzoyl-2,5-dimethylpyrrol-1-yl)ethyl phenyl sulfoxide (410):

In 15 ml of methylene chloride was dissolved 589 mg (1.76 mmoles) of 2-(3-benzoyl-2,5-dimethylpyrrol-1-yl)ethyl phenyl sulfide, and 350 mg (1.72 mmoles) of m-chloroperbenzoic acid (85% purity) was added. The mixture was stirred at room temperature for 16 hours. The organic layer was washed with a 1.0 N aqueous solution of sodium hydroxide, and then water, dried, and concentrated, and chromatographed on a column of silic gel using benzene/ethyl acetate as an eluent to afford compound (410)(562 mg, 1.60 mmoles, 91%).

IR (CHCl$_3$ solution): 1631, 1572, 1510, 1475, 1445, 1415, 1369, 1086, 1044 cm$^{-1}$. NMR (CDCl$_3$, δ(ppm): 2.20 (3H, s, CH$_3$ at the 5position of the pyrrole ring), 2.42 (3H, s, CH$_3$ at the 2-position of the pyrrole ring), 2.77–3.3 (2H, m, —CH$_2$S(O)—), 3.9–4.6 (2H, m, —NCH$_2$—), 6.02 (1H, s, H on the pyrrole ring), 7.2–7.9 (10H, m, Ph).

EXAMPLE 44

In the same way as in Example 43, compound (408) and (412) were synthesized.

EXAMPLE 45

Synthesis of 2-(3-benzoyl-2,5-dimethylpyrrol-1-yl)-2-methylethyl phenyl sulfone (414):

Compound (414) was prepared by oxidation at −78° C. for 20 hours using 2.0 equivalents of m-perbenzoic acid in the same way as in Example 43.

IR (CHCl$_3$ solution): 1630, 1570, 1510, 1475, 1445, 1415, 1369, 1330, 1140, 1085 cm$^{-1}$. NMR (CDCl$_3$, δ(ppm)): 2.20 (3H, s, CH$_3$ at the 5-position of the pyrrole ring), 2.43 (3H, s, CH$_3$ at the 2-position of the pyrrole ring), 2.7–3.4 (2H, m, —CH$_2$SO$_2$—), 3.9–4.6 (2H, m, —NCH$_2$—), 6.03 (1H, s, H on the pyrrole), 7.2–7.9 (10H, m, Ph).

EXAMPLE 46

Synthesis of 2-(3-benzoyl-2,5-dimethylpyrrol-1-yl)propionaldehyde (502):

Dimethylsulfoxide (625 mg, 8 mmoles) was dissolved in 20 ml of methylene chloride, and the solution was cooled to −78° C. with a dry ice-acetone bath. Oxalyl chloride (762 mg, 6 mmoles) was added to the solution, and the mixture was stirred at the same temperature for 30 minutes. Then, 1.027 g (4 mmoles) of 2-(3-benzoyl-2,5-dimethylpyrrol-1-yl)-2-methylethanol dissolved in 12 ml of methylene chloride was added dropwise to the mixture. The mixture was stirred for 30 minutes, and then 1.6 ml of triethylamine was added dropwise. The mixture was warmed up gradually to room temperature. The reaction mixture was shaken with 50 ml of methylene chloride and 50 ml of water to separate an organic layer. The organic layer was washed with water and a saturated aqueous solution of sodium chloride, and dried over anhydrous sodium sulfate. The solvent was distilled off under reduced pressure to form a dark scarlet oil. The oil was chromatographed on a column containing 50 g of silica gel using benzene/ethyl acetate (20/1) as an eluent. The fractions were collected each in an amount of 50 ml. From the 5th to 14th fractions, 500 mg (50%) of compound (502) was obtained.

IR (neat): 2740, 1741, 1630, 1600, 1512, 1445, 1410, 1246, 903, 722, 690 cm$^{-1}$.

NMR (CDCl$_3$, δ(ppm)): 1.51 (3H, d, J=7 Hz, CHCH$_3$), 2.08 (3H, s, CH$_3$ at the 5-position of the pyrrole ring), 2.45 (3H, s, CH$_3$ at the 2-position of the pyrrole ring), 4.72 (1H, q, J=7 Hz, CHCH$_3$), 6.17 (1H, s, H on the pyrrole ring), 7.3–7.6 (3H, m, H on Ph), 7.7–7.9 (2m, H on Ph), 9.79 (1H, s, CHO).

EXAMPLE 47

In the same way as in Example 46, compounds (500), (504) and (506) were synthesized.

EXAMPLE 48

Synthesis of 1-(3-benzoyl-2,5-dimethylpyrrol-1-yl)-2-propanone (600):

Benzoic anhydride (4.52 g, 20.0 mmoles) and 0.2 ml of 52% aqueous hydriodic acid were added to 1.65 g (10.0 mmoles) of 3-(2,5-dimethylpyrrol-1-yl)-2-butanone, and the mixture was reacted at 100° C. The reaction mixture was worked up, and then chromatographed on a column of silica gel to afford compound (600) (510 mg, 1.9 mmoles, 19%).

NMR (CDCl$_3$, δ(ppm)): 1.53 (3H, d, J=6 Hz, CHCH$_3$), 2.10 (3H, s, COCH$_3$), 2.13 (3H, s, CH$_3$ at the 5-position of the pyrrole ring), 2.53 (3H, s, CH$_3$ at the 2-position of the pyrrole ring), 4.73 (1H, q, J=6 Hz, NCHCO), 6.03 (1H, s, H on the pyrrole ring), 7.2–7.5 (3H, m, H on Ph), 7.6–7.8 (2H, m, H on Ph).

EXAMPLE 49

In the same way as in Example 48, compound (602) was synthesized.

EXAMPLE 50

Synthesis of ethyl 2-(3-benzoyl-2,5-dimethylpyrrol-1-yl)propionate (706):

To ethyl 2-(2,5-dimethylpyrrol-1-yl)propionate (975 mg, 5.0 mmoles) and benzoic anhydride (3.39 g, 15.0 mmoles) was added 0.2 ml of 52% aqueous hydriodic acid, and the reaction as performed at 130° C. for 3 hours in atmosphere of nitrogen. To the reaction mixture was added 50 ml of 5% sodium hydroxide and the resulting mixture was extracted with 100 ml of ethyl acetate. The separated organic layer was washed, dried, and concentrated to afford 1.55 g of a crude product. The product was chromatographed on a column of silica gel using cyclohexane/ethyl acetate (3/1) as an eluent to afford compound (706) (670 mg, 2.24 mmoles, 44.8%).

IR (neat): 3050, 2980, 2940, 1740, 1630, 1600, 1575, 1515, 1450, 1415, 1380, 1300, 1250, 1220, 1200, 1175, 1160, 1110, 1070, 1040, 1025, 1015, 985, 930, 910, 860, 805, 790 730, 695, 670 cm$^{-1}$.

NMR (CDCl$_3$, δ(ppm)): 1.17 (3H, t, J=8 Hz, CH$_2$CH$_3$), 1.59 (3H, d, J=7 Hz, CHCH$_3$), 2.10 (3H, s, CH$_3$ at the 5-position of the pyrrole ring), 2.50 (3H, s, CH$_3$ at the 2-position of the pyrrole ring), 4.16 (2H, q, J=8 Hz, CH$_2$CH$_3$), 4.92 (1H, q, J=7 Hz, CHCH$_3$), 6.04 (1H, s, H on the pyrrole ring), 7.23–7.50 (3H, m, H on Ph), 7.63–7.87 (2H, m, H on Ph).

Mass spectrum (70 eV; m/e, %): 300 (M+1, 13), 299 (M+, 66), 298 (37), 284 (3), 270 (3), 266 (21), 224 (10)

222 (13), 198 (43), 197 (39), 194 (18) 183 (8), 148 (6), 122 (8), 120 (11), 106 (9), 105 (100), 77 (50), 51 (9), 42 (9), 39 (10).

EXAMPLE 51

Synthesis of methyl 2-(3-benzoyl-2,5-dimethylpyrrol-1-yl)propionate (704):

In the same way as in Example 50, compound (704) was prepared:

IR (neat): 3030, 2970, 2940, 1740, 1630, 1600, 1575, 1515, 1445, 1415, 1375, 1300, 1250, 1200, 1110, 1070, 1045, 910, 860, 810, 790, 730, 700 cm$^{-1}$.

NMR (CCl$_4$, δ(ppm)): 1.57 (3H, d, J=7 Hz, CH$_3$CHCOO—), 2.07 (3H, s, CH$_3$ at the 5-position of the pyrrole ring), 2.43 (3H, s, CH$_3$ at the 2-position of the pyrrole ring), 3.67 (3H, s, —COOCH$_3$), 4.88 (1H, q, J=7 Hz, NCHCOO—), 5.92 (1H, s, H at the 4-position of the pyrrole ring), 7.40 and 7.70 (3H and 2H, m, —COPh).

EXAMPLE 52

Synthesis of methyl 2-(3-p-chlorobenzoyl-2,5-dimethylpyrrol-1yl)propionate (726):

Compound (726) was prepared in the same way as in Example 50.

IR (neat): 2980, 2950, 1745, 1630, 1590, 1520, 1485, 1420, 1380, 1300, 1250, 1200, 1175, 1110, 1090, 1070, 1040, 1015, 960, 915, 845, 810, 760, 730, 700 cm$^{-1}$.

NMR (CDCl$_3$, δ(ppm)): 1.67 (3H, d, J=7 Hz, CH$_3$CHCOO—), 2.16 (3H, s, CH$_3$ at the 5-position of the pyrrole ring), 2.53 (3H, s, CH$_3$ at the 2-position of the pyrrole ring), 3.80 (3H, s, —COOCH$_3$), 5.01 (1H, d, J=7 Hz, NCHCOO—), 6.06 (1H, s, H at the 4-position of the pyrrole ring), 7.53 and 7.90 (2H×2, d, J=9 Hz, H on Ph).

EXAMPLE 53

Synthesis of ethyl 3-benzoyl-2,5-dimethylpyrrol-1-ylacetate (702):

Compound (702) was prepared in the same way as in Example 50.

IR (neat): 3030, 2950, 2900, 1745, 1630, 1600, 1570, 1520, 1445, 1420, 1370, 1250, 1210, 1050, 1025, 900, 730, 695 cm$^{-1}$.

NMR (CCl$_4$, δ(ppm)): 1.23 (3H, t, J=7 Hz, —COOCH$_2$CH$_3$), 2.10 (3H, s, CH$_3$ at the 5-position of the pyrrole ring), 2.41 (3H, s, CH$_3$ at the 2-position of the pyrrole ring), 4.13 (2H, q, J=7 Hz, —COOCH$_2$CH$_3$), 4.43 (2H, s, N—CH$_2$—COO—), 5.93 (1H, s, H at the 4-position of the pyrrole ring), 7.35 and 7.66 (3H and 2H, m, —COPh).

EXAMPLE 54

Synthesis of methyl 2-(3-nicotinoyl-2,5-dimethylpyrrol-1-yl)propionate (728):

Nicotinoyl chloride hydrochloride (2.14 g, 12 mmoles) was reacted with methyl 2-(2,5-dimethylpyrrol-1-yl)-pripionate (1.81 g, 10 mmoles) in the presence of 1.60 g (12 mmoles) of aluminum chloride in 30 ml of carbon disulfide by heating them under reflux for 3 hours. The carbon disulfide was distilled off under reduced pressure, and 10 ml of an aqueous solution of sodium hydrogen carbonate was added to the residue. The mixture was stirred at room temperature for 1 hour, and acidified with dilute hydrochloric acid. The aqueous layer was extracted with 50 ml of ethyl acetate three times. The organic layer was washed with an aqueous solution of sodium hydrogen carbonate, dried over anhydrous magnesium sulfate, and concentrated under reduced pressure to afford 1.31 g of a crude product. The product was chromatographed on a column of silica gel using cyclohexane/ethyl acetate (1/1) as an eluent to afford 450 mg (1.57 mmoles, 15.7%) of methyl 2-(3-nicotinoyl-2,5-dimethylpyrrol-1-yl)propionate.

IR (neat): 2980, 2940, 1740, 1630, 1585, 1510, 1415, 1380, 1300, 1260, 1225, 1200, 1110, 1070, 1040, 1025, 960, 910, 860, 825, 810, 750, 730, 710, 695 cm$^{-1}$.

NMR (CDCl$_3$, δ(ppm)): 1.65 (3H, d, J=7 Hz, CH$_3$CHCOO—), 2.15 (3H, s, CH$_3$ at the 5-position of the pyrrole ring), 2.55 (3H, s, CH$_3$ at the 2-position of the pyrrole ring), 3.73 (3H, s, —COOCH$_3$), 5.02 (1H, q, J=7 Hz, NCHCOO—), 6.07 (1H, s, H at the 4-position of the pyrrole ring), 7.50, 8.10, 8.73, 9.05, (1H×4, m, H on the pyridine ring).

EXAMPLE 55

Synthesis of ethyl 3-(2-theonyl)-2,5-dimethylpyrrol-1-ylacetate (730);

In the same way as in Example 54, compound (730) was prepared in a yield of 12.4%.

IR (neat): 3100, 3000, 2940, 1750, 1615, 1580, 1525, 1420, 1380, 1260, 1210, 1105, 1050, 1030, 890, 880, 840, 760, 725 cm$^{-1}$.

NMR (CDCl$_3$, δ(ppm)): 1.23 (3H, t, J=7 Hz, —COOCH$_2$CH$_3$), 2.16 (3H, s, CH$_3$ at the 5-position of the pyrrole ring), 2.47 (3H, s, CH$_3$ at the 2-position of the pyrrole ring), 4.20 (2H, q, J=7 Hz, —COOCH$_2$CH$_3$), 4.56 (2H, s, NCH$_2$COO—), 6.40 (1H, s, H at the 4-position of the pyrrole ring), 7.10, 7.60, 7.78 (1H×3, dd×3, H on the thiophene ring).

EXAMPLE 56

Synthesis of benzyl 2-(3-benzoyl-2,5-dimethylpyrrol-1-yl)propionate (720):

In 5 ml of methylene chloride was dissoved 2-(3-benzoyl-2,5-dimethylpyrrol-1-yl)propionic acid (500 mg, 1.85 mmoles), and 257 μl (1.85 mmoles) of triethylamine was added. The mixture was stirred at −15° C. for 5 minutes. Isobutyl chloroformate (243 μl, 1.85 mmoles) was added to the solution, and the mixture stirred at −15° C. for 10 minutes. Then, 190 μl (1.85 mmoles) of benzyl alcohol was added. The mixture was stirred at room temperature for 20 hours, and 50 ml of methylene chloride was added. The organic layer was washed with water, dilute hydrochloric acid and an aqueous solution of sodium hydrogen carbonate in this order, dried, and concentrated to afford 543 mg of a crude product. The product was chromatographed on a column of silica gel using benzene/ethyl acetate as an eluent to afford compound (720)(421 mg, 1.16 mmoles, 63%).

IR (neat): 1747, 1630, 1518, 1416, 1250, 910, 728, 693 cm$^{-1}$.

NMR (CDCl$_3$, δ(ppm)): 1.65 (3H, d, J=7 Hz, CHCH$_3$), 2.07 (3H, s, CH$_3$ at the 5-position of the pyrrole ring), 2.46 (3H, s, CH$_3$ at the 2 position of the pyrrole ring), 4.97 (1H, q, J=7 Hz, CHCH$_3$), 5.19 (2H, s, OCH$_2$Ph), 6.07 (1H, s, H on the pyrrole ring), 7.30 (5H, s, OCH$_2$Ph), 7.4 (3H, m, H on Ph), 7.8 (2H, m, H on Ph).

EXAMPLE 57

Synthesis of phenyl 2-(3-benzoyl-2,5-dimethylpyrrol-1-yl)propionate (710):

In the same way as in Example 56, compound (710) was prepared in a yield of 80%

IR (neat): 1765, 1630, 1516, 1415, 1250, 1190, 908, 712 cm$^{-1}$.

NMR (CDCl$_3$, δ(ppm)): 1.75 (3H, d, J=7 Hz, CH$CH_3$), 2.23 (3H, s, CH$_3$ at the 5-position of the pyrrole ring), 2.62 (3H, s, CH$_3$ at the 2-position of the pyrrole ring), 5.18 (1H, q, J=7 Hz, $C$HCH$_3$), 6.10 (1H, s, H on the pyrrole ring), 6.9–7.6 (8H, m, H on Ph), 7.7–7.9 (2H, m, H on Ph).

EXAMPLE 58

In the same way as in Example 56, compounds (700), (708), (712), (714), (716), (718), (722), (724), (732), (734), (736) and (738) were synthesized.

EXAMPLE 59

Synthesis of 2-(3-benzoyl-2,5-dimethylpyrrol-1-yl)propionamide (802):

Compound (802) was prepared in a yield of 78.5% by the same method via a mixed acid anhydride as in Example 56 except that aqueous ammonium hydroxide was used instead of benzyl alcohol.

IR (neat): 3430, 3380, 3230, 3000, 2960, 1740, 1695, 1635, 1610, 1580, 1520, 1450, 1420, 1380, 1300, 1250, 1200, 1180, 1160, 1115, 1075, 1050, 1030, 1000, 985, 935, 910, 850, 810, 790, 730, 700 cm$^{-1}$.

NMR (CDCl$_3$, δ(ppm)): 1.57 (3H, d, J=7 Hz, CH$CH_3$), 2.13 (3H, s, CH$_3$ at the 5-position of the pyrrole ring), 2.48 (3H, s, CH$_3$ at the 2-position of the pyrrole ring), 4.85 (1H, g, J=7 Hz, $C$HCH$_3$), 6.03 (1H on the pyrrole ring), 6.20 and 6.80 (1H×2, bs×2, NH$_2$), 7.25–7.50 (3H, m, H on Ph), 7.55–7.85 (2H, m, H on Ph).

EXAMPLE 60

Synthesis of N-phenyl-2-(3-benzoyl-2,5-dimethylpyrrol-1-yl)propionamide (808):

Compound (808) was prepared in a yield of 60.7% by using aniline in the same way as in Example 59.

Melting point: 165°–166° C. (recrystallized from cyclohexane).

IR (KBr): 3360, 3290, 3240, 3160, 3090, 3010, 2950, 2880, 1705, 1685, 1630, 1610, 1570, 1550, 1520, 1505, 1450, 1415, 1390, 1330, 1300, 1250, 1210, 1190, 1180, 1160, 1125, 1110, 1075, 1035, 1025, 985, 970, 930, 910, 835, 820, 810, 800, 790, 760, 720, 690, 675 cm$^{-1}$.

NMR (CDCl$_3$, δ(ppm)): 1.63 (3H, d, J=7 Hz, CH$CH_3$), 2.14 (3H, s, CH$_3$ at the 5-position of the pyrrole ring), 2.50 (3H, s, CH$_3$ at the 2-position of the pyrrole ring), 4.97 (1H, q, J=7 Hz, $C$HCH$_3$), 6.09 (1H, s, H on the pyrrole ring), 7.0–7.8 (11H, m, Ph×2 and NH).

EXAMPLE 61

In the same way as in Example 59, compound (806) was prepared in a yield of 17.2% by using diethylamine in the same way as in Example 59.

IR (neat): 3500, 3070, 3000, 2950, 1725, 1660, 1635, 1605, 1580, 1515, 1450, 1415, 1380, 1365, 1290, 1265, 1250, 1220, 1190, 1175, 1160, 1100, 1070, 1035, 1025, 1000, 980, 930, 910, 890, 805, 790, 730, 695, 675 cm$^{-1}$.

NMR (CDCl$_3$, δ(ppm)): 0.76 and 1.13 (3H×2, t×2, J=7 Hz, CH$_2$$CH_3$), 1.51 (3H, d, J=7 Hz, CH$CH_3$), 2.16 (3H, s, CH$_3$ at the 5-position of the pyrrole ring), 2.56 (3H, s, CH$_3$ at the 2-position of the pyrrole ring), 3.02 and 3.36 (2H×2, q×2, J=7 Hz, $CH_2$CH$_3$), 4.91 (1H, q, J=7 Hz, $C$HCH$_3$), 6.04 (1H, s, H on the pyrrole ring), 7.30–7.50 (3H, m, H on Ph). 7.65–7.85 (2H, m, H on Ph).

EXAMPLE 62

Synthesis of 2-(3-benzoyl-2,5-dimethylpyrrol-1-yl)propionylmorpholine (816):

In the same way as in Example 59, compound (816) was prepared in a yield of 23.5% by using morpholine.

IR (neat): 3100, 3020, 2960, 2900, 1750, 1665, 1640, 1610, 1580, 1520, 1450, 1420, 1390, 1370, 1300, 1275, 1255, 1240, 1195, 1180, 1160, 1120, 1075, 1050, 1030, 935, 915, 850, 810, 800, 735, 700, 680 cm$^{-1}$.

NMR (CDCl$_3$, δ(ppm)): 1.53 (3H, d, J=7 Hz, CH$CH_3$), 2.13 (3H, s, CH$_3$ at the 5-position of the pyrrole ring), 2.51 (3H, s, CH$_3$ at the 2-position of the pyrrole ring), 2.8–3.4 (4H, m, N$CH_2$C), 3.60 (4H, bs, C$CH_2$O), 4.86 (1H, q, J=7 Hz, $C$HCH$_3$), 6.04 (1H, s, H on the pyrrole ring), 7.30–7.50 (3H, H on Ph), 7.60–7.80 (2H, m, H on Ph).

EXAMPLE 63

Synthesis of N'-phenyl-2-(3-benzoyl-2,5-dimethylpyrrol-1-yl)propiohydrazide (824):

In the same way as in Example 59, compound (824) was prepared in a yield of 78% by using phenylhydrazine.

NMR (CDCl$_3$, δ(ppm)): 1.60 (3H, d, J=7 Hz, CH$CH_3$), 2.13 (3H, s, CH$_3$ at the 5-position of the pyrrole ring), 2.49 (3H, s, CH$_3$ at the 2-position of the pyrrole ring), 4.91 (1H, q, J=7 Hz, $C$HCH$_3$), 6.10 (1H, s, H on the pyrrole ring), 6.4–8.0 (12H, m, Ph×2 and NHNH).

EXAMPLE 64

In the same way as in Example 59, compounds (800), (804), (810), (812), (814) (818), (820) and (822) were synthesized.

EXAMPLE 65

Synthesis of 2-(3-benzoyl-2,5-dimethylpyrrol-1-yl)propionaldehyde diethyl acetal (904):

Ethyl orthoformate (2 ml) and one drop of conc. sulfuric acid were added to 257 mg (1.0 mmole) of 2-(3-benzoyl-2,5-dimethylpyrrol-1-yl)propionaldehyde, and the reaction was performed at room temperature for 5 hours. Ether was added, and the organic layer was washed with water, dried, concentrated and chromatographed on a column of silica gel to afford compound (904) (82 mg, 0.25 mmole, 25%).

IR (neat): 1625, 1570, 1506, 1444, 1413 cm$^{-1}$.

EXAMPLE 66

In the same way as in Example 65, compounds (900), (902) and (906) to (914) were prepared.

EXAMPLE 67

Activity of inhibiting platelet aggregation (inhibitory effect of drugs on platelet aggregation) in vitro:

Some 1-substituted-3-acylpyrrole derivatives and other drugs were tested for platelet aggregation inhibiting activities in vitro using platelet-rich plasmas (PRP) of man and guinea pigs. The results are shown as minimum concentration of drugs which inhibit more than 50% of platelet aggregation induced by several aggregating agents.

In experiments with PRP of guinea pigs, sodium arachidonate (final concentration 0.03 mM) was used as an aggregating agent. In experiments with human PRP, sodium arachidonate (final concentration 0.1 mM), collagan suspension (final concentration 10 μg/ml), epinephrine solution (final concentration 20 μg/ml; for secondary aggregation), an epinephrine solution (final concentration 2 μg/ml; for primary aggregation) and ADP (final concentration 5 μM) were used as aggregating agents.

The results are shown in Table 1 (experiments with guinea pig PRP) and Table 2 (experiments with human PRP).

Preparation of PRP, drugs, and aggregating agents (1) Preparation of PRP (platelet-rich plasma)

In an experiment with guinea pig PRP, citrated blood (containing 0.38% sodium citrate as a final concentration) was withdrawn by cardiac puncture from Hartley-strain male guinea pigs having a body weight of 350 to 600 g. The citrated blood was centrifuged at 1,000 rpm for 10 minutes at room temperature, and the supernatant platelet suspension (PRP) was separated.

The PRP was stored at room temperature, and used as soon as possible. Those which had been stored for more than 4 hours after preparation were not used.

In the experiment using human PRP, heapinized blood (containing 20 IU/ml of heparin) was taken from the cubital vein of healthy volunteers, and centrifuged at 1,000 rpm at room temperature for 10 minutes. The supernatant platelet suspension (PRP) was separated.

(2) Preparation of drugs

For each test, a drug is dissolved in dimethylsulfoxide to a concentration of 10 mg/ml, and diluted with physiological saline to form 1 ml each of solutions having a concentration of 2500 μg/ml, 1000 μg/ml, 750 μg/ml, 500 μg/ml, 250 μg/ml and 100 μg/ml. A compound having a free carboxylic acid as a residue such as indomethacine and Ibprofen was dissolved in 0.1 M NaHCO$_3$ to form a sodium salt solution having a concentration of 10 mg/ml. Then, the solution was diluted with physiological saline in the same way as above to form a test drug solution.

When the test drug in a concentration of 100 μg/ml (corresponding to 10 μg/ml as a final concentration) completely inhibited platelet aggregation in this test, it was further diluted with physiological saline to a concentration of 75 μg/ml, 50 μg/ml, 25 μg/ml, and 10 μg/ml, and each diluted solution was further tested for platelet aggregation inhibiting activities.

(3) Preparation of aggregating agents

Sodium arachidonate

Arachidonic acid (99% pure, a product of Sigma Co., Ltd.) was dissolved in 0.1 M NaHCO$_3$, and a 3.3 mM solution of sodium arachidonate was prepared. The solution was diluted with physiological saline to a concentration of 1 mM and used in the experiments. The 3.3 mM solution was stored in a refrigerator as a stock solution, and the 1 mM solution was newly prepared from the stock solution every time it was used.

Collagen suspension

The collagen suspension (made by Hormon-Chemie, West Germany) was diluted with physiological saline to a concentraton of 100 μg/ml.

Epinephrine solution

Epinephrine hydrogen tartarate was dissolved in physiological saline to form solutions having a concentration of 200 μg/ml (corresponding to a final concentration of 2 μg/ml).

ADP solution

Disodium salt of ADP was dissolved in a 0.1 M trishydrochloric acid buffer to form a 50 μM solution (corresponding to a final concentraton of 5 μM).

Test method for measuring an activity inhibiting platelet aggregation (1) Determination of the degree of platelet aggregation in a control experiment:

Physiological saline (50 μl) and 50 μl of the aggregating agent solution were added to 400 μl of PRP which had been pre-warmed and stirred at 37° C. in a quvett set in a holder of an aggregometer. Platelet aggregation was thus initiated, and the change of light transmittance through a stirred platelet suspension was recorded for 3 minutes by a recorder joined to the aggregometer. An increase in transmittance after 3 minutes ($T_0$) was used as a parameter of the rate of platelet aggregation in control experiments.

(2) Determination of the effect of the drug on platelet aggregation:

To 400 μl of PRP in a quvett was added 50 μl of a test drug solution. The mixture was pre-incubated and stirred for 2 minutes at 37° C. Then 50 μl of the aggregating agent was added to drug containing PRP and again aggregation responses were recorded as increases in light transmittance after 3 minutes ($T_1$) in the same way as in (1) above. Percent inhibition was calculated from the formula $$\text{Percent inhibition} = 100 \times \frac{(T_0 - T_1)}{T_0}$$

The minimum concentration (expressed as a final concentration) of the drug which showed a percent inhibition of more than 50% was shown as IC$_{50}$.

For the above in vitro test for the inhibition of platelet aggregation, reference may be had to H. M. Davis, J. Phyllis, K. Paul and W. Terry: Thromb. Res. 11, 217–226 (1977) and R. E. Anderson and J. G. Foulks: Thromb. Haemos. 36, 343–359 (1976).

TABLE 1

| | (Guinea pigs PRP) | |
|---|---|---|
| No. | 1-Substituted-3-acylpyrrole derivative (compound No.) | IC$_{50}$ (μg/ml) |
| 1. | 100 | 5 |
| 2. | 102 | 5 |

TABLE 1-continued

| No. | 1-Substituted-3-acylpyrrole derivative (compound No.) | $IC_{50}$ (μg/ml) |
|---|---|---|
| | (Guinea pigs PRP) | |
| 3. | 110 | 1 |
| 4. | 108 | 5 |
| 5. | 306 | 7.5 |
| 6. | 314 | 1 |
| 7. | 328 | 2.5 |
| 8. | 310 | 2.5 |
| 9. | 206 | 2.5 |
| 10. | 218 | 5 |
| 11. | 404 | 2.5 |
| 12. | 706 | 1 |
| 13. | 802 | 5 |
| 14. | 238 | 10 |
| 15. | 252 | 2.5 |
| Comp. 1 | (structure: phenyl-C(=O)- pyrrole with CH₃ groups and N—CHCH₂CH₃) | 0.75 |
| Comp. 2 | Indomethacine | 5 |

TABLE 2

| No. | Compound | $IC_{50}$ (μg/ml) Aggregation by | | | | |
|---|---|---|---|---|---|---|
| | | Arachidonate (0.1 mM) | Collagen (10 μg/ml) | Epinephrine Primary (2 μg/ml) | Epinephrine Secondary (20 μg/ml) | ADP (5 μM) |
| 1 | 1-substituted 3-acylpyrrole-derivative | 0 | 10 | 10 | 1 | 10 |
| Comparison | Indomethacine | 1 | 10 | 10 | 1 | 10 |

EXAMPLE 68

Inhibitory effect on prostaglandin biosynthesis in vitro:

Sprangue-Dawley rats (male, 180–200 g) were fasted overnight, and killed by blow on the head. The stomach was isolated, and fundus stomach strips were prepared. The smooth muscle strips were perfused with Krebs-Hensleit solution (gassed with 95% $O_2$+5% $CO_2$ gas) of 37° C. at a rate of 5 ml/ml. The Krebs-Hensleit solution contained 0.1 μg/ml of atropine, 0.1 μg/ml of phenoxybenzamine, 3 μg/ml of propranolol, 0.1 μg/ml of tripelennamine, and 0.2 μg/ml of methylsergide to prevent the effect of smooth muscle contracting substances, and 1 μg/ml of indomethacine to inhibit the biosynthesis of prostaglandin by the smooth muscles. Then, 150 μl of a reaction solution containing biologically synthesized prostaglandin was added to the perfusion solution, and the amount of the biologically synthesized prostaglandin was measured from the contraction of the smooth muscles. The contraction of the smooth muscles was recorded on a recorder using an isotonic transducer.

The reaction solution containing biologically synthesized prostaglandin was prepared in the following manner.

To 0.4 mg/ml of microsomes of the seminal vesicle of bovine were added 5 mM of L-tryptophan, 0.025 μM of bovine hemoglobin and 3 mμ of glutathione as cofactors. The mixture was incubated together with each of the test compounds shown in Table 4 at 37° C. for 2 minutes, and immediately then, 4 μg/ml of sodium arachidonate was added. The mixture was further incubated at 37° C. for 10 minutes, and immediately then, the prostaglandin activity of the reaction solution was measured by bioassay.

The microsomes of the seminal vesicle of bovine had been prepared by suspending microsomes of the seminal vesicle of bovine (a product of Miles Laboratories, Inc.) in a 50 mM Tris.HCl buffer (pH 7.4) using a glass homogenizer, and stored in ice water prior to use.

The results are shown in Table 3. $ID_{50}$ denotes the concentration of each test compound required to inhibit the biosynthesis of prostaglandins by 50%.

TABLE 3

| No. | 1-Substituted-3-acylpyrrole derivative (Compound No.) | $ID_{50}$ (μg/ml) |
|---|---|---|
| 1. | 102 | 11.9 |
| 2. | 100 | 145.3 |
| 3. | 306 | 5.6 |
| 4. | 314 | 56.0 |
| 5. | 310 | 11.5 |
| 6. | 206 | 18.4 |
| 7. | 706 | 20.0 |
| Comp. 1 | | 145.0 |
| Comp. 2 | 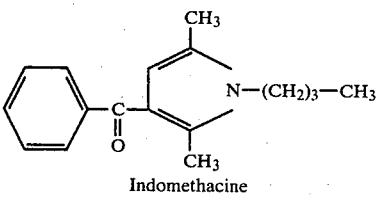 | 0.6 |
| | Indomethacine | |

EXAMPLE 69

Inhibitory effect of compounds on platelet aggregation in extra vivo:

The effect of the compounds shown in Table 4 on platelet aggregation was assessed using guinea pig in extra vivo.

Each of the test compounds was dissolved in propylene glycol so that its concentration became 100 mg/ml (dosage corresponded to 100 mg/kg) and 30 mg/ml (dosage corresponded to 30 mg/kg). The drug solution was administered either orally or subcutaneously to Hartley-strain guinea pigs (3 per group) having a body weight of 300 to 350 g. As a control, propylene glycol was administered. One hour after the administration, citrated blood was taken out by cardiac puncture, and centrifuged to obtain PRP (see Example 67).

In the case of oral administration, the animals had been fasted overnight.

The percent inhibitions of the test compounds were measured as follows:

Into a quvett set in a holder of an aggregometer and prewarmed at 37° C. with stirring, was put 450 μl of the above PRP, and then 50 μl of an aggregating agent was added. The aggregation curve was recorded for an additional 3 minutes, and an increase in light transmittance through PRP after 3 minutes (T$_B$) was recorded (see Example 67). As a control, an increase of transmittance of PRP taken from a guinea pig group administered with propylene glycol alone (T$_A$) was recorded in the same way above. The percent inhibitions were calculated in accordance with the following equation.

$$\text{Percent inhibition} = 100 \times \frac{(T_A - T_B)}{T_A}$$

As the aggregating agent, sodium arachidonate (a final concentraton of 0.03 mM) and a collagen suspension (a final concentration of 5 μg/ml) were used.
The results are shown in Table 4.

polyethylene glycol so as to provide a volume of 2 ml/kg) was orally administered. One hour later, 0.1 ml of 1% carrageenan (dissolved in physiological saline) as an inflammation-inducing substance was subcutaneously injected to the paw of the left hind leg. A control group was orally administered with 2 ml/kg of polyethylene glycol. As a positive control, 25 mg/kg of Ibprofen was similarly administered. Three hours after the injection of 1% carrageenan, the volume of the left leg was measured, and the ratio of edema was calculated from the volume before the administration of the carrageenan. The percent inhibition of edema in comparison with the control group was determined.
The results are shown in Table 5.

TABLE 5

| No. | 1-Substituted-3-acylpyrrole derivative (compound No.) | Dosage (mg/kg) | Percent inhibition of edema |
|---|---|---|---|
| 1. | 102 | 100 | 8 |
| 2. | 306 | 100 | 16 |
| 3. | 206 | 100 | 10 |
| Comp. 1 | (structure) | 100 | 10 |
| Comp. 2 | Ibprofen | 25 | 51 |

EXAMPLE 71

Acute toxicity:

ICR male mice with a body weight of 24 to 27 g (5 to 6 per group) were used. Each test compound was dis-

TABLE 4

| No. | 1-Substituted-3-acylpyrrole derivative (compound No.) | Dosage (mg/kg) | Administration route | Percent inhibition of platelet aggregation | |
|---|---|---|---|---|---|
| | | | | Sodium arachidonate | Collagen |
| 1. | 102 | 100 | PO | 54–89 | 29–55 |
| 2. | 102 | 10 | SC | 99 | 79 |
| 3. | 110 | 100 | PS | 96 | 90 |
| 4. | 108 | 100 | " | 62 | 14 |
| 5. | 306 | 100 | " | 62 | 34 |
| 6. | 206 | 100 | + | 90 | 97 |
| 7. | 802 | 100 | " | 100 | 40 |
| Com. 1 | (structure) | 100 | " | 0 | 0 |
| Comp. 2 | Acetylsalicylic acid | 100 | " | 77 | 41 |

The percent inhibitions in the above table are averages of three guinea pigs. For details of the above extra vivo test about inhibition of platelet aggregation, the literature references described in Example 67 may be referred to.

EXAMPLE 70

Antiinflammatory activity:

Sprangue-Dawley (SD) male rats with a body weight of 160 to 180 g, four in each group, were used. The volume of the left leg was measured, and each of the test compounds shown in Table 5 (100 mg/kg dissolved in solved in propylene glycol in various concentrations, and administered orally (in a volume of 0.1 to 0.05 ml/10 g), subcutaneously (in a volume of 0.1 to 0.05 ml/10 g), or intraperitoneally (in a volume of 0.05 ml/10 g) to the mice. The behavior, mortality, etc. of the animals were observed for 10 days. The LD$_{50}$ (50% lethal dose) of each test compound was determined by the Litchfield-Wilcoxon method.

When compound (102) was used as the test compound, the results were as shown in Table 6.

TABLE 6

| Administration route | Dosages (mg/kg) | | | | LD$_{50}$ (mg/kg) |
|---|---|---|---|---|---|
| | 4000 | 3000 | 2000 | 1000 | |
| Perorul | 1/6 | 0/6 | 0/6 | 0/6 | >4000 |
| Subcutaneous | 0/5 | | | | >4000 |
| | 500 | 250 | 125 | 62.5 | |
| Intraperitoneal | 5/5 | 5/5 | 4/5 | 0/5 | 110 |

The denominator indicates the number of mice used, and the numerator, the number of dead mice.

EXAMPLE 72

Formulation of tablets:

Tablets were prepared each of which had the following composition.

| Active ingredient | 200 mg |
|---|---|
| Lactose | 280 mg |
| Potato starch | 80 mg |
| Polyvinyl pyrrolidone | 11 mg |
| Magnesium stearate | 5 mg |
| | 576 mg |

The active ingredient, lactose and potato starch were mixed, and the mixture uniformly wetted with a 20% ethanol solution of polyvinyl pyrrolidone. The wet mixture was passed through a 2.0 mm-mesh sieve, and dried at 45° C., and again passed through a 1.5 mm-mesh sieve. The granules obtained were mixed with magnesium stearate, and the mixture compressed into tablets.

As representative active ingredients, compounds (100) and (102) were used respectively.

EXAMPLE 73

Formulation of capsules:

Hard gelatin capsules were produced each of which had the following recipe.

| Active ingredient | 200 mg |
|---|---|
| Microcrystalline cellulose | 195 mg |
| Amorphous silica | 5 mg |
| | 400 mg |

The active ingredient in a finely divided form, the microcrystalline cellulose and the unpressed amorphous silica were fully mixed, and packed into hard gelatin capsules.

As representative active ingredients, compounds (100) and (102) were used respectively. No substantial trouble occurred during manufacture.

EXAMPLE 74

Ampoules were prepared each of which had a capacity of 5 ml and contained the following ingredients in the proportions indicated.

| Active ingredient | 200 mg |
|---|---|
| Polyethylene glycol 600 | 200 mg |
| Distilled water to make | 5 ml |

The active ingredient and polyethylene glycol were dissolved in water in an atomsphere of nitrogen. The solution was boiled, and cooled under a nitrogen atomsphere, and distilled. Pre-treated water was added to the solution to the desired capacity, and filtered aseptically. The above manufacturing operation was performed under scattered light. Filling of the solution was carried out in a stream of nitrogen, and sterilization was performed by heating at 121° C. for 20 minutes.

As representative active ingredients, compounds (100) and (102) were used.

What we claim is:

1. 1-Substituted-3-benzoylpyrrole derivatives of the formula

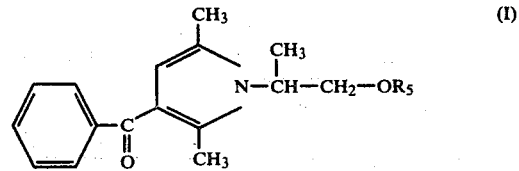

wherein $R_5$ represents a hydrogen atom or a lower alkyl group with 1 to 4 carbon atoms.

2. A 1-substituted derivative of claim 1, viz., 2-(3-benzoyl-2,5-dimethylpyrrol-1-yl)-2-methylethyl methyl ether.

3. A platelet aggregation inhibiting agent comprising an effective amount of the 1-substituted-3-acylpyrrole derivative of claim 1 and a pharmaceutically acceptable carrier or diluent.

* * * * *